US009604050B2

(12) United States Patent
Barker

(10) Patent No.: US 9,604,050 B2
(45) Date of Patent: Mar. 28, 2017

(54) SYSTEMS AND METHODS FOR PERCUTANEOUSLY IMPLANTING INTO A PATIENT A PADDLE LEAD OF AN ELECTRICAL STIMULATION SYSTEM

(71) Applicant: BOSTON SCIENTIFIC NEUROMODULATION CORPORATION, Valencia, CA (US)

(72) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 238 days.

(21) Appl. No.: 14/622,210

(22) Filed: Feb. 13, 2015

(65) Prior Publication Data

US 2015/0231388 A1    Aug. 20, 2015

Related U.S. Application Data

(60) Provisional application No. 61/942,455, filed on Feb. 20, 2014.

(51) Int. Cl.
*A61N 1/05* (2006.01)
*A61B 17/34* (2006.01)
*A61B 17/00* (2006.01)

(52) U.S. Cl.
CPC ........ *A61N 1/0504* (2013.01); *A61B 17/3401* (2013.01); *A61B 17/3468* (2013.01);
(Continued)

(58) Field of Classification Search
CPC ............ A61B 17/3401; A61B 17/3415; A61B 17/3468; A61B 2017/00946; A61B 2017/3445; A61N 1/0504; A61N 1/0553
See application file for complete search history.

(56) References Cited

U.S. PATENT DOCUMENTS 3,330,278 A    7/1967 Santomieri
3,359,978 A    12/1967 Smith
(Continued)

FOREIGN PATENT DOCUMENTS

EP    2008686    12/2008
WO    89/00436   1/1989
WO    03011361   2/2003

OTHER PUBLICATIONS

U.S. Appl. No. 62/153,844, filed Apr. 28, 2015.

*Primary Examiner* — Amanda Patton
(74) *Attorney, Agent, or Firm* — Lowe Graham Jones PLLC; Bruce E. Black

(57) ABSTRACT

A multi-needle paddle lead introducer includes a needle assembly, a hub assembly, and a sheath. The needle assembly includes at least one primary needle and at least one secondary needle. The secondary needle is coupled to the primary needle along a portion of the longitudinal length of the needle assembly such that the primary needle and the secondary needle are arranged in a side-by-side configuration. The secondary needle is configured and arranged to move relative to the primary needle along the longitudinal length of the needle assembly. The hub assembly includes a primary needle hub coupled to a proximal end portion of the primary needle and a secondary needle hub coupled to a proximal end portion of the primary needle. The sheath is configured and arranged for disposing over a portion of an outer surface of the needle assembly and for sliding along the longitudinal length of the needle assembly.

20 Claims, 16 Drawing Sheets

(52) U.S. Cl.
CPC ........ *A61N 1/0553* (2013.01); *A61B 17/3415* (2013.01); *A61B 2017/00946* (2013.01); *A61B 2017/3445* (2013.01)

(56) References Cited

U.S. PATENT DOCUMENTS

| | | | |
|---|---|---|---|
| 3,568,660 A | 3/1971 | Crites et al. | |
| 3,677,243 A | 7/1972 | Nerz | |
| 4,355,646 A | 10/1982 | Kallok et al. | |
| 4,449,973 A | 5/1984 | Luther | |
| RE31,855 E | 3/1985 | Osborne | |
| 4,512,351 A | 4/1985 | Pohndorf | |
| 4,608,986 A | 9/1986 | Beranek et al. | |
| 4,808,157 A | 2/1989 | Coombs | |
| 5,125,904 A | 6/1992 | Lee | |
| 5,320,602 A | 6/1994 | Karpiel | |
| 5,380,290 A | 1/1995 | Makower et al. | |
| 5,409,469 A | 4/1995 | Schaerf | |
| 5,441,504 A | 8/1995 | Pohndorf et al. | |
| 5,616,227 A | 4/1997 | McCormick | |
| 5,713,867 A | 2/1998 | Morris | |
| 5,741,233 A | 4/1998 | Riddle et al. | |
| 5,752,937 A | 5/1998 | Otten et al. | |
| 5,755,693 A | 5/1998 | Walker et al. | |
| 5,931,863 A | 8/1999 | Griffin, III et al. | |
| 6,080,141 A | 6/2000 | Castro et al. | |
| 6,181,969 B1 | 1/2001 | Gord | |
| 6,251,119 B1 | 6/2001 | Addis | |
| 6,358,460 B1 | 3/2002 | Hunt, Jr. et al. | |
| 6,454,744 B1 | 9/2002 | Spohn et al. | |
| 6,494,860 B2 | 12/2002 | Rocamora et al. | |
| 6,516,227 B1 | 2/2003 | Meadows et al. | |
| 6,582,390 B1 | 6/2003 | Sanderson | |
| 6,609,029 B1 | 8/2003 | Mann et al. | |
| 6,609,032 B1 | 8/2003 | Woods et al. | |
| 6,641,564 B1 | 11/2003 | Kraus | |
| 6,645,178 B1 | 11/2003 | Junker et al. | |
| 6,712,791 B2 | 3/2004 | Lui et al. | |
| 6,741,892 B1 | 5/2004 | Meadows et al. | |
| 6,749,600 B1 | 6/2004 | Levy | |
| 6,758,854 B1 | 7/2004 | Butler et al. | |
| 6,869,416 B2 | 3/2005 | Windheuser et al. | |
| 6,939,327 B2 | 9/2005 | Hall et al. | |
| 7,001,396 B2 | 2/2006 | Glazier et al. | |
| 7,014,626 B2 | 3/2006 | Sanderson | |
| 7,101,353 B2 | 9/2006 | Lui et al. | |
| 7,192,433 B2 | 3/2007 | Osypka et al. | |
| 7,244,150 B1 | 7/2007 | Brase | |
| 7,359,755 B2 | 4/2008 | Jones et al. | |
| 7,437,193 B2 | 10/2008 | Parramon | |
| 7,524,305 B2 | 4/2009 | Moyer | |
| 7,672,734 B2 | 3/2010 | Anderson | |
| 7,744,571 B2 | 6/2010 | Fisher et al. | |
| 7,761,165 B1 | 7/2010 | He | |
| 7,887,733 B2 | 2/2011 | Moyer | |
| 7,909,798 B2 | 3/2011 | Osypka | |
| 7,938,806 B2 | 5/2011 | Fisher et al. | |
| 7,941,227 B2 | 5/2011 | Barker | |
| 7,949,395 B2 | 5/2011 | Kuzma | |
| 7,974,706 B2 | 7/2011 | Moffitt et al. | |
| 7,985,232 B2 | 7/2011 | Potter et al. | |
| 7,993,305 B2 | 8/2011 | Ye et al. | |
| 8,043,263 B2 | 10/2011 | Helgeson et al. | |
| 8,105,287 B2 | 1/2012 | Fisher et al. | |
| 8,105,315 B2 | 1/2012 | Johnson et al. | |
| 8,112,159 B2 | 2/2012 | Harris et al. | |
| 8,147,456 B2 | 4/2012 | Fisher et al. | |
| 8,175,710 B2 | 5/2012 | He | |
| 8,224,450 B2 | 7/2012 | Brase | |
| 8,273,059 B2 | 9/2012 | Nardeo et al. | |
| 8,348,899 B2 | 1/2013 | Chesnin et al. | |
| 8,364,278 B2 | 1/2013 | Pianca et al. | |
| 8,377,006 B2 | 2/2013 | Tal et al. | |
| 8,382,715 B2 | 2/2013 | Nardeo et al. | |
| 2002/0111617 A1 | 8/2002 | Cosman et al. | |
| 2005/0021119 A1 | 1/2005 | Sage et al. | |
| 2005/0055027 A1 | 3/2005 | Yeung et al. | |
| 2005/0107861 A1 | 5/2005 | Harris et al. | |
| 2005/0113860 A1 | 5/2005 | Keidar | |
| 2007/0150036 A1 | 6/2007 | Anderson | |
| 2008/0300538 A1 | 12/2008 | Schweikert et al. | |
| 2009/0248111 A1 | 10/2009 | Pianca et al. | |
| 2009/0254019 A1 | 10/2009 | Gehl et al. | |
| 2009/0259283 A1 | 10/2009 | Brandt et al. | |
| 2011/0054402 A1 | 3/2011 | Tanabe et al. | |
| 2011/0218549 A1 | 9/2011 | Barker | |
| 2011/0224680 A1 | 9/2011 | Barker | |
| 2011/0224681 A1 | 9/2011 | McDonald | |
| 2011/0230893 A1 | 9/2011 | Barker | |
| 2012/0209285 A1 | 8/2012 | Barker et al. | |
| 2012/0323254 A1 | 12/2012 | Bonde et al. | |
| 2013/0053851 A1 | 2/2013 | Schmitz et al. | |
| 2014/0039586 A1* | 2/2014 | Barker | A61N 1/0551 607/116 |
| 2014/0073926 A1 | 3/2014 | Rajendran et al. | |
| 2014/0276927 A1 | 9/2014 | Barker | |
| 2015/0073431 A1 | 3/2015 | Barker | |
| 2015/0073432 A1 | 3/2015 | Barker | |

* cited by examiner

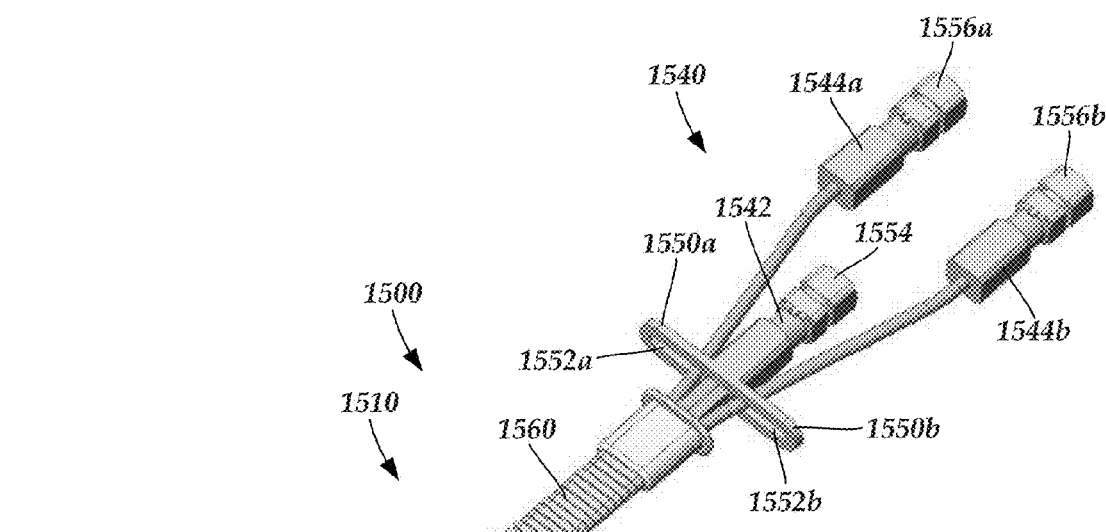
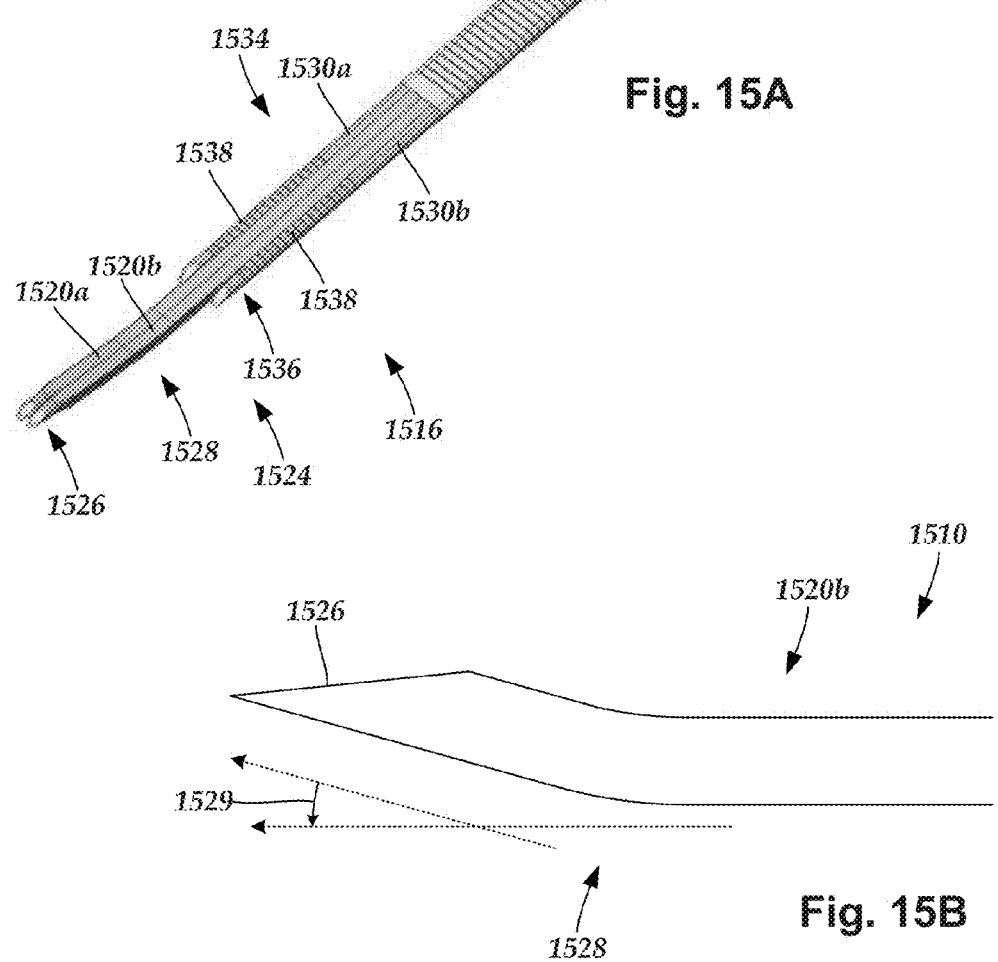
Fig. 15A
Fig. 15B

SYSTEMS AND METHODS FOR PERCUTANEOUSLY IMPLANTING INTO A PATIENT A PADDLE LEAD OF AN ELECTRICAL STIMULATION SYSTEM

CROSS-REFERENCE TO RELATED APPLICATIONS

This application claims the benefit under 35 U.S.C. §119 (e) of U.S. Provisional Patent Application Ser. No. 61/942,455, filed Feb. 20, 2014, which is incorporated herein by reference.

FIELD

The present invention is directed to the area of implantable electrical stimulation systems and methods of making and using the systems. The present invention is also directed to a multi-needle paddle lead introducer suitable for percutaneously implanting paddle leads of electrical stimulation systems into a patient, as well as methods of making and using the multi-needle paddle lead introducers and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a multi-needle paddle lead introducer includes a needle assembly having at least one primary needle and at least one secondary needle. The primary needle has an outer surface, a longitudinal length, a proximal end portion, a distal end portion, and a sharpened distal tip. The primary needle also defines a lumen extending along the longitudinal length of the primary needle. The secondary needle is coupled to the primary needle along a portion of the longitudinal length of the needle assembly such that the primary needle and the secondary needle are arranged in a side-by-side configuration. The secondary needle has an outer surface, a longitudinal length, a proximal end portion, a distal end portion, and a sharpened distal tip. The secondary needle defines a lumen extending along the longitudinal length of the secondary needle. The secondary needle is suitable for moving relative to the primary needle along the longitudinal length of the needle assembly. A hub assembly is coupled to the needle assembly. The hub assembly includes at least at least one primary needle hub and at least one secondary needle hub. The primary needle hub is coupled to the proximal end portion of the primary needle and the secondary needle hub is coupled to the proximal end portion of the secondary needle. The introducer further includes a sheath having an outer surface and a longitudinal length. The sheath is suitable for disposing over at least a portion of the outer surface of the needle assembly and for sliding along the longitudinal length of the needle assembly.

In another embodiment, an insertion kit includes the multi-needle paddle lead introducer, as discussed above, and a paddle lead suitable for insertion into a patient using the lead introducer. The paddle lead includes at least one lead body, a paddle body, electrodes, terminals, and conductors. The lead body has a distal end portion, a proximal end portion, and a longitudinal length. The paddle lead is attached to the distal end portion of the at least one lead body. The electrodes are disposed along the paddle body. The terminals are disposed along the proximal end portion of the at least one lead body. The conductors electrically couple the electrodes to the terminals.

In yet another embodiment, a method of implanting a paddle lead into a patient includes providing the multi-needle paddle lead introducer, discussed above. The method includes inserting the at least one primary needle of the multi-needle paddle lead introducer into the patient. The distal tip of the at least one primary needle is advanced to a target insertion location in proximity to a target stimulation location within the patient. The at least one secondary needle of the multi-needle paddle lead introducer is advanced relative to the at least one primary needle until the distal tip of the at least one secondary needle is disposed at the target insertion location. The distal end portion of the sheath of the multi-needle paddle lead introducer is advanced to the target insertion location along the longitudinal lengths of the at least one primary needle and the at least one secondary needle. The at least one primary needle and the at least one secondary needle are removed from the patient while leaving the distal end portion of the sheath inserted into the target insertion location. The paddle lead is advanced to the target insertion location within a lumen of the sheath. The sheath is removed from the patient leaving a paddle body of the paddle lead disposed in the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 15A is a schematic perspective view of another embodiment of primary needles, secondary needles, a hub assembly, and a sheath of a multi-needle paddle lead introducer, the secondary needles flanking the primary needles and retracted relative to the primary needles, the primary needles collectively forming a bend along distal end portions of the primary needles and the secondary needles configured to slide distally along the bend relative to the primary needles, according to the invention;

FIG. 15B is a schematic side view of one embodiment of a bend formed along the distal end portion of one of the primary needles of FIG. 15A, according to the invention;

DETAILED DESCRIPTION

The present invention is directed to the area of implantable electrical stimulation systems and methods of making and using the systems. The present invention is also directed to a multi-needle paddle lead introducer suitable for percutaneously implanting paddle leads of electrical stimulation systems into a patient, as well as methods of making and using the multi-needle paddle lead introducers and electrical stimulation systems.

Suitable implantable electrical stimulation systems include, but are not limited to, a least one lead with one or more electrodes disposed along a distal end of the lead, and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
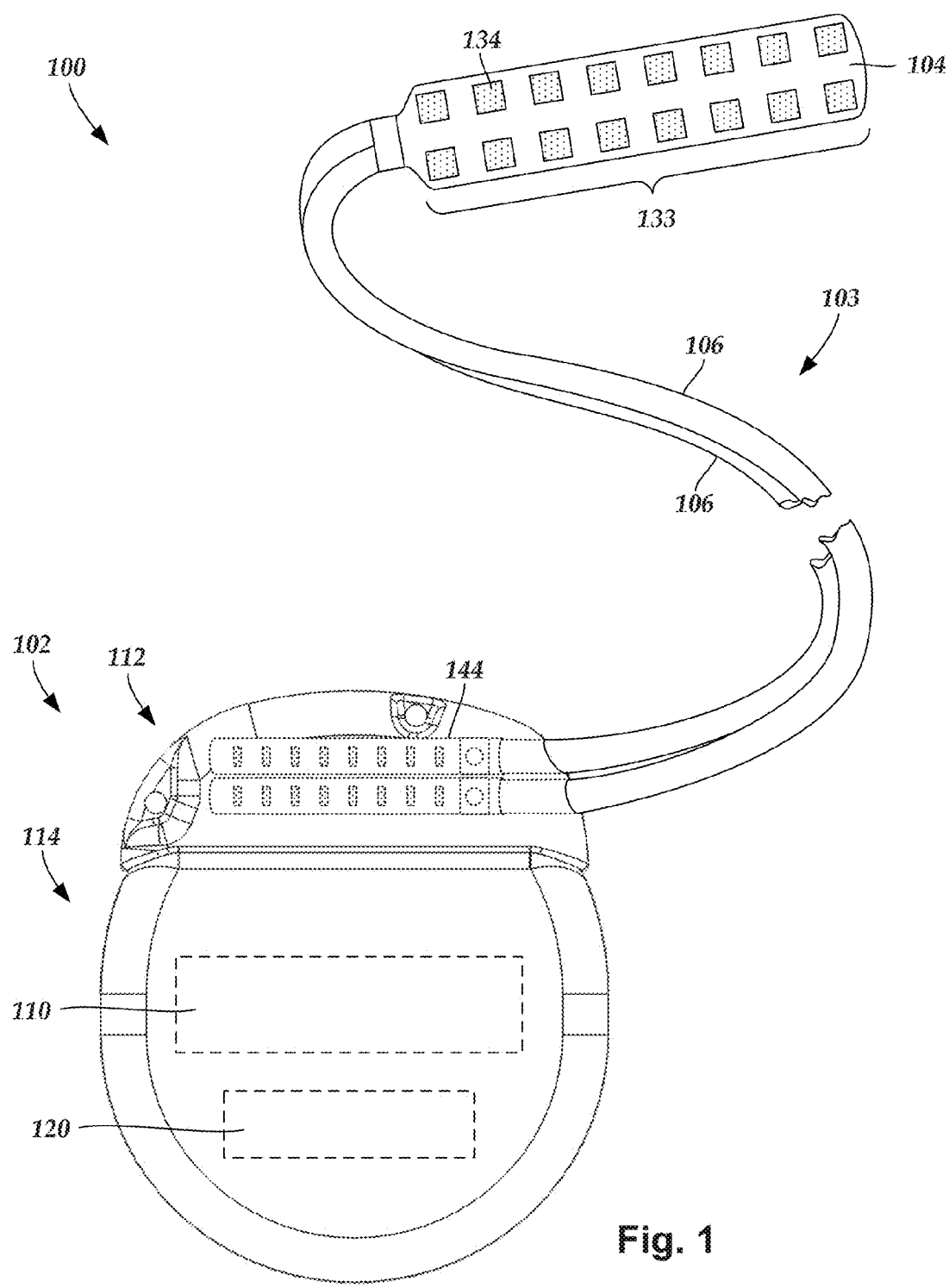
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. The electrodes 133 are disposed along a paddle body 104 attached to a distal end portion of the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. In the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is suitable for making an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
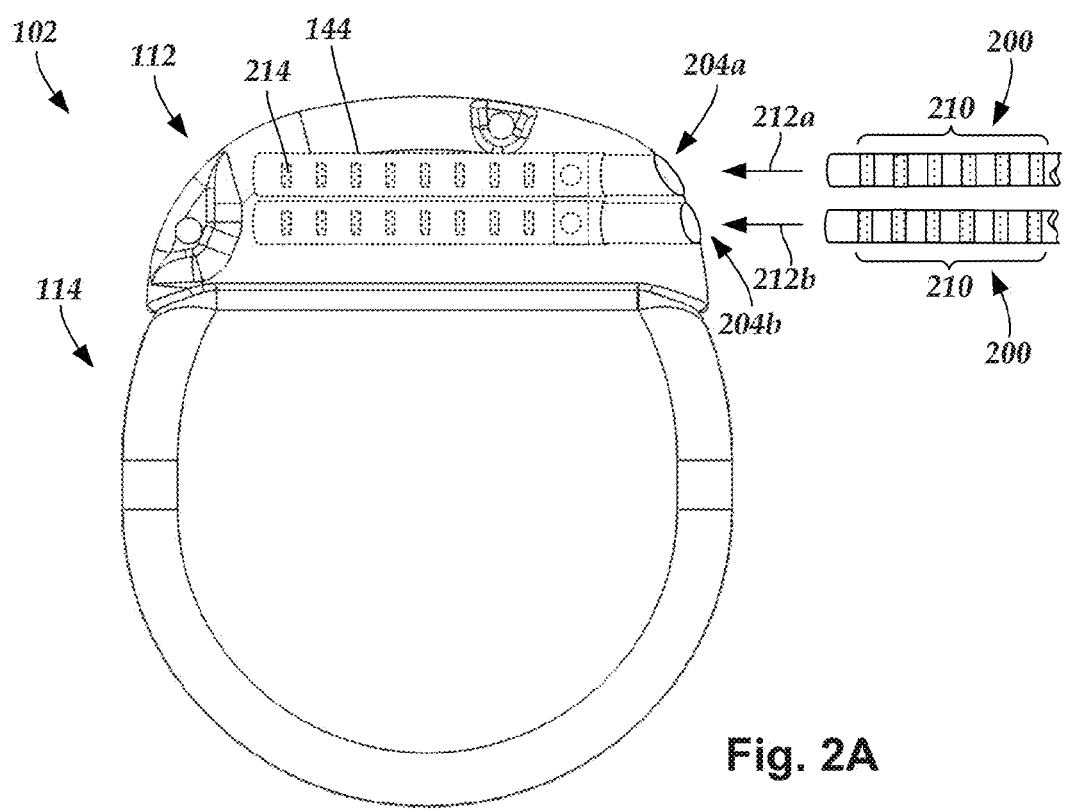
FIG. 2A is a schematic view of one embodiment of the control module of FIG. 1 configured and arranged to electrically couple to an elongated device, according to the invention.
Figure 2B:
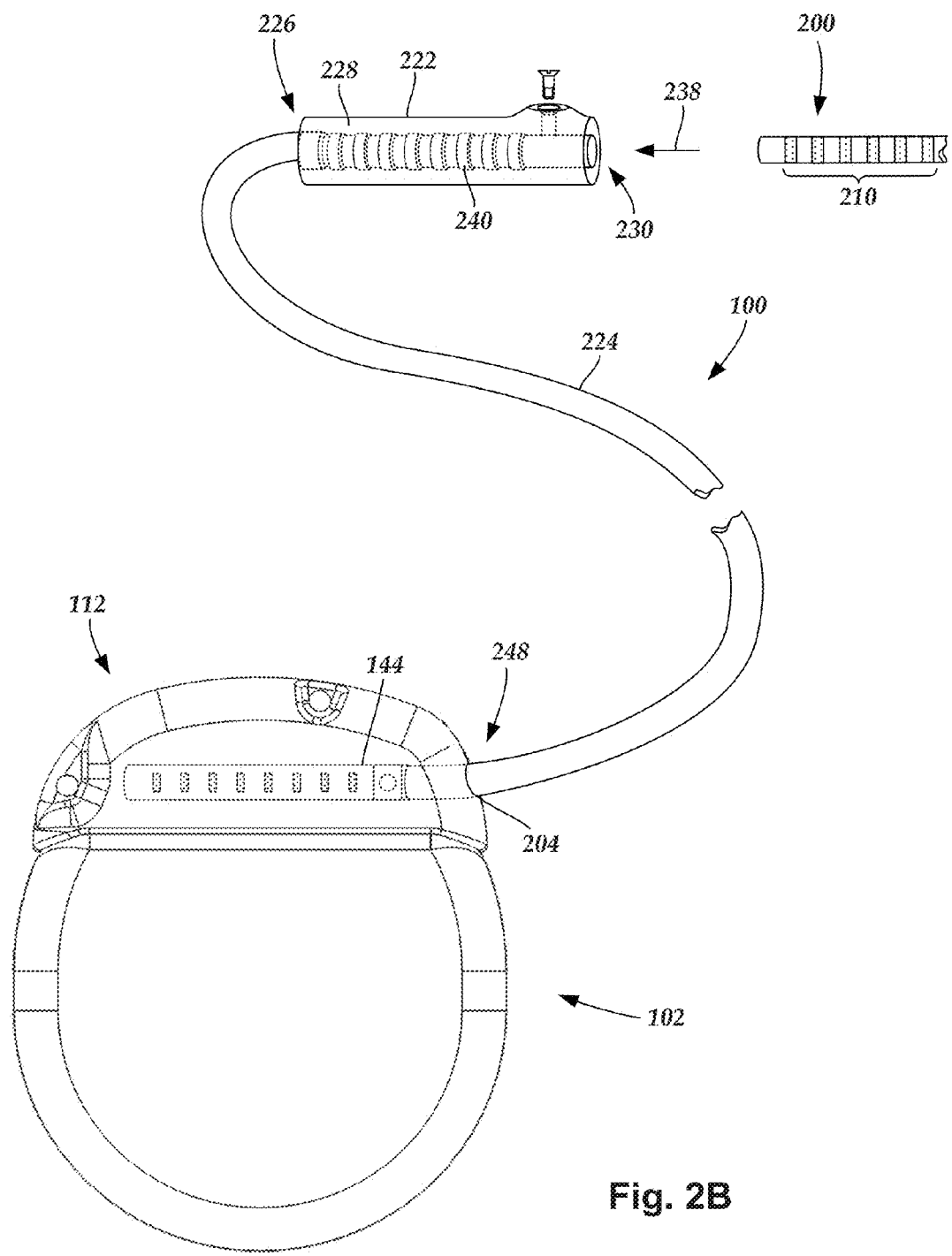
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 suitable for coupling to one embodiment of the control module connector 144. The one or more elongated devices may include, for example, the lead body 106, one or more intermediate devices (e.g., the lead extension 224 of FIG. 2B, a splitter, an adaptor, or a combination thereof).

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is suitable for coupling one or more elongated devices 200

(e.g., one or more lead bodies 106, splitters, adaptors, lead extensions, or the like or combinations thereof) to the control module 102. In FIG. 2B, the lead extension 224 is shown coupled to a single port 204 defined in the control module connector 144. Additionally, the lead extension 224 is shown coupled to a single elongated device 200. In alternate embodiments, the lead extension 224 is suitable for coupling to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is suitable for insertion into a connector disposed in another lead extension (or another intermediate device). In other embodiments (and as shown in FIG. 2B), the proximal end 248 of the lead extension 224 is suitable for insertion into the control module connector 144.

Due to the size and shape of paddle bodies, paddle leads are typically surgically implanted (e.g., via a laminotomy, a laminectomy, or the like) into a patient. Surgically implanting paddle leads into patients can be invasive. For example, in the case of surgical implantation of the paddle leads into the epidural space, the associated procedure may include surgical removal of bony arches or the spinous process on one or more vertebrae. Removal of such anatomical features may cause complications including, for example, risk of trauma, prolonged healing time, patient discomfort, risk of infection, and the like.

As herein described, a multi-needle paddle lead introducer ("introducer") facilitates percutaneous implantation of the paddle leads into the patient. Implanting a paddle lead percutaneously may be less invasive than conventional surgical paddle-lead-implantation techniques (e.g., a laminotomy or a laminectomy). The introducer can be used to implant a paddle lead using multiple needles and a sheath. In at least some embodiments, the introducer uses multiple epidural needles. In at least some embodiments, the multiple needles include one or more primary needles and one or more secondary needles, where the primary needle(s) initiate a path through patient tissue, and where the secondary needle(s) enlarge the path formed by the primary needle(s). In at least some embodiments, the paddle lead is implanted via the sheath, which is inserted into the path formed by the multiple primary and secondary needles.

Figure 3A:
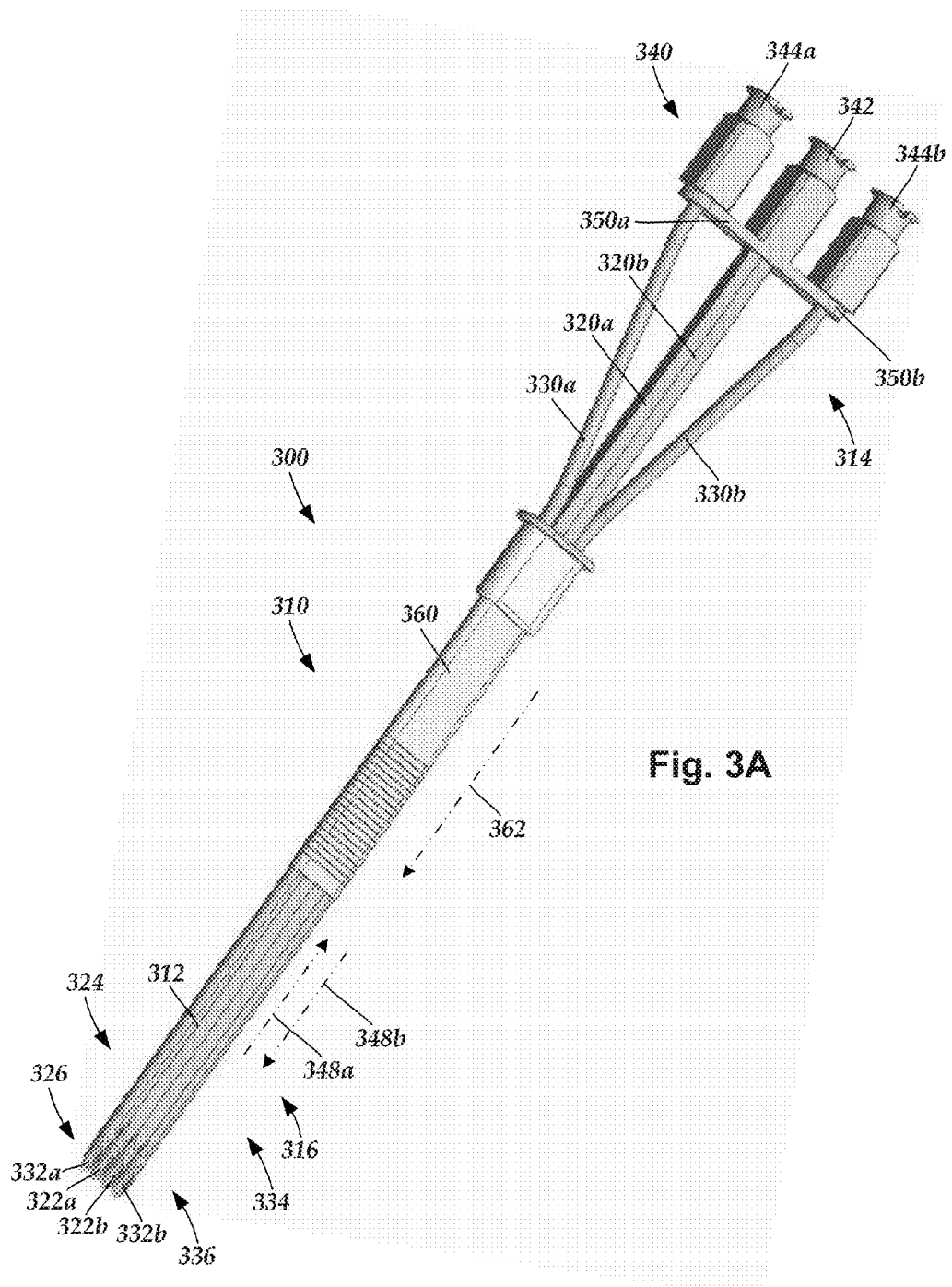
FIG. 3A is a schematic perspective view of one embodiment of a needle assembly, a hub assembly, and a sheath of a multi-needle paddle lead introducer, the needle assembly including two primary needles flanked by secondary needles, according to the invention.
Figure 3B:
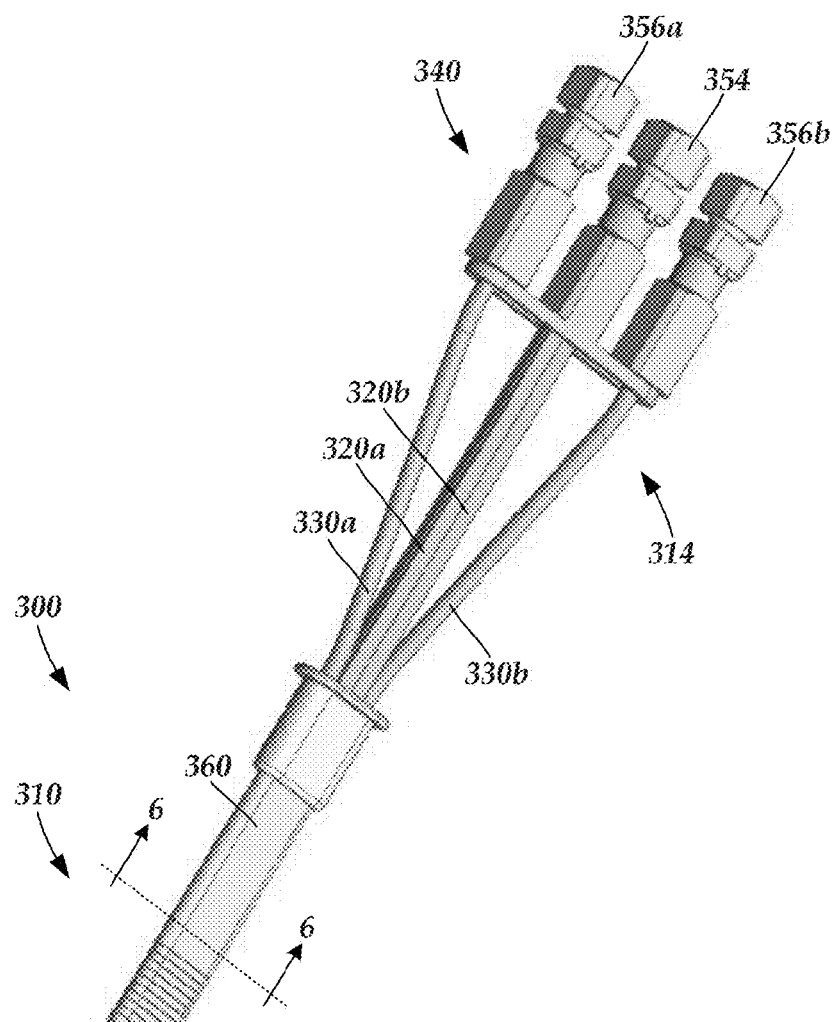
FIG. 3B is a schematic perspective view of one embodiment of the needle assembly of FIG. 3A with stylets inserted into primary and secondary needles of the needle assembly, according to the invention.

FIGS. 3A-3B illustrate, in perspective view, one embodiment of an introducer 300. The introducer 300 includes a needle assembly 310, a hub assembly 340, and a sheath 360. The needle assembly 310 has an outer surface 312, a proximal end portion 314, a distal end portion 316, and a longitudinal length extending between the proximal end portion 314 and the distal end portion 316. In at least some embodiments, the proximal end portion 314 is coupled to the hub assembly 340.

The needle assembly 310 includes at least one primary needle and at least one secondary needle. In the illustrated embodiment, the at least one primary needle includes a first primary needle 320a and a second primary needle 320b, and the at least one secondary needle includes a first secondary needle 330a and a second secondary needle 330b. Although the needle assembly 310 is shown as including two primary needles 320a, it will be understood that the needle assembly 310 can include any suitable number of primary needles including, for example, one, two, three, four, or more primary needles. Similarly, although the needle assembly 310 is shown as including two secondary needles, a first secondary needle 330a, and a second secondary needle 330b. It will be understood that the needle assembly 310 can include any suitable number of secondary needles including, for example, one, two, three, four, or more secondary needles.

Any suitable number of primary and secondary needles can be used in combination with one other. For example, the introducer 300 can include either an equal number of primary needles and secondary needles, more primary needles than secondary needles, or fewer primary needles than secondary needles. The primary needles 320a, 320b and the secondary needles 330a, 330b are positioned in a side-by-side configuration and are in physical contact with one another along at least a portion of the longitudinal length of the needle assembly 310. In at least some embodiments, at least one of the needles of the needle assembly 310 is coupled directly to the hub assembly 340 at the proximal end portion 314 of the needle assembly 310.

The primary and secondary needles can be formed from any material suitable for insertion into a patient including, for example, one or more metals (e.g., stainless steel, titanium, or the like), one or more alloys, one or more shape memory materials, one or more plastic resins, or the like.

Each of the one or more primary needles of the needle assembly 310 defines one or more lumens extending along the length of the needle assembly 310. In at least some embodiments, each of the one or more primary needles defines at least one lumen that also extends along at least a portion of the hub assembly 340. In at least some embodiments, at least one of the secondary needles of the needle assembly 310 defines one or more lumens extending along the length of the needle assembly 310. In at least some embodiments, each of the one or more secondary needles defines at least one lumen that also extends along at least a portion of the hub assembly 340. In at least some embodiments, each of the needles defines one or more lumens extending along the length of the needle assembly 310.

In FIG. 3A (and in other figures), each of the needles 320a, 320b, 330a, and 330b defines a single lumen 322a, 322b, 332a, and 332b, respectively, extending along the entire longitudinal length of the needle assembly 310. It will be understood that each needle of the needle assembly 310 may include any suitable number of lumens including, for example, two, three, four, or more needle lumens.

In at least some embodiments, the needles 320a, 320b, 330a, and 330b have bore sizes of 14-gauge. In at least some other embodiments, the bore sizes of the needle lumens are, for example, 19-gauge, 18-gauge, 17-gauge, 16-gauge, 15-gauge, 14-gauge, 13-gauge, 12-gauge, 11-gauge, 10-gauge, or larger. In at least some embodiments, the needle assembly 310 includes multiple needles, where at least one of the needles has a bore size that is different from the bore size of at least one other of the needles. In other embodiments, each of the needles of the needle assembly 310 has the same bore size.

The needles of the needle assembly 310 each include distal end portions having distal tips. In FIG. 3A, the primary needles 320a, 320b are shown having distal end portions 324 with distal tips 324. Similarly, the secondary needles 330a, 330b are shown having distal end portions 334 with distal tips 336. The distal tips 326, 336 are preferably sharpened to facilitate piercing into, and advancing through, patient tissue during insertion of the introducer 300 into a patient. It may be advantageous to facilitate the ability of the needles to advance through patient tissue by using a lubricant (e.g., silicone, or the like) or forming the needles from a lubricious material (e.g., one or more fluoropolymers, or the like).

The one or more secondary needles are designed to move relative to the one or more primary needles along the longitudinal length of the needle assembly 310, as shown by directional arrows 348a, 348b. In some embodiments, the secondary needles can move either proximally or distally relative to the primary needles. In other embodiments, the secondary needles can only move in one direction relative to the primary needles. The introducer can be manufactured with the distal tips of the secondary needles longitudinally even with the primary needles. Alternately, the introducer can be manufactured with the secondary needles refracted (or advanced) relative to the primary needles.

The hub assembly 340 includes a primary needle hub 342 coupled to the proximal end portion of the primary needles 320a, 320b and secondary needle hubs 344a, 344b coupled to the proximal end portions of the secondary needles 330a, 330b, respectively. In at least some embodiments, each needle of the needle assembly has a separate and distinct hub from the remaining needles of the needle assembly. In at least some other embodiments, multiple primary needles 320a, 320b are coupled to a single primary needle hub 342, thereby providing a common access (e.g., for one or more stylets) to the lumens 322a, 322b of the primary needles 320a, 320b, respectively. In at least some embodiments, the two secondary needles 330a, 330b are coupled to individual hubs 344a, 344b, providing an independent access (e.g., for one or more stylets) to the lumens 332a, 332b of the two secondary needles 330a, 330b, respectively.

In some embodiments, the primary needle hub 342 includes a connection assembly suitable for coupling the secondary needle hubs 344a, 344b to the primary needle hub 342. In at least some embodiments, the connection assembly includes one or more slots defined in one or more tabs. In FIG. 3A (and in other figures), the primary needle hub 342 includes a first tab 350a and a second tab 350b extending outwards from opposing sides of the primary needle hub 342. Each tab 350a, 350b defines a slot (652a, 652b, respectively, in FIG. 6) suitable for receiving the secondary needles 330a, 330b, respectively.

In at least some embodiments, the slots 652a, 652b are sized such that the secondary needles 330a, 330b, respectfully, can move relative to the primary needle hub 342 along the longitudinal length of the needle assembly 310. In at least some embodiments, the slots 652a, 652b are sized such that the secondary needle hubs 344a, 344b are prevented from passing through the slots 652a, 652b. In which case, the slots 652a, 652b control the distance along which the secondary needles 330a, 330b, respectfully, can move distally relative to the primary needles 320a, 320b. Thus, in at least some embodiments the slots 652a, 652b can prevent the distal tips 336 of the secondary needles 330a, 330b, respectfully, from extending beyond a distal-most location relative to the primary needles 320a, 320b, respectfully. For example, in at least some embodiments the slots 652a, 652b prevent the distal tips 336 of the secondary needles 330a, 330b, respectfully, from extending distally to the distal tips 326 of the primary needles 320a, 320b, respectfully.

In at least some embodiments, at least one of the needle hubs 342, 344a, 344b includes a proximal female Luer hub assembly suitable for receiving a Luer tip syringe. The Luer tip syringe may be employed for injecting or withdrawing fluid or air during insertion of the introducer 300. For example, during insertion of the introducer 300, fluid (e.g., saline solution, air, or the like) may be introduced or removed through the hub assembly 340 to check for positioning of the distal tips 326 and 336 of the introducer 300 (e.g., in an epidural space of the patient). In at least some embodiments, the proximal ends of the secondary needles 330a, 330b bend away from the primary needles 320a, 320b to provide clearance for attaching a syringe to the hub assembly 340.

The hub assembly 340 can be formed from any material suitable for insertion into a patient including, for example, one or more metals (e.g., stainless steel, titanium, or the like), one or more alloys, one or more shape memory materials, one or more plastic resins, or the like. Other molding or formation techniques can also be used. The hub assembly 340 can be coupled to the one or more needles in any suitable manner including, for example, welding, bonding, brazing, insert molding (e.g., using an insert molded thermoplastic), or the like or combinations thereof.

The hub assembly 340 and one or more of the needle lumens 322a, 322b, 332a, 332b may be suitable for receiving one or more stylets. The stylet(s) may be suitable for preventing tissue coring, when the needle assembly 310 is advanced through patient tissue. Such coring can cause undesired patient trauma. Additionally, such coring can also clog needle lumens, thereby preventing subsequent performance of loss-of-resistance tests.

In FIG. 3B, stylets 354, 356a, and 356b are shown inserted into the needle lumens. In particular, as shown in FIG. 3B, the stylets 354 are inserted into the lumens 322a, 322b of the primary needle 320a, 320b, while the stylets 356a, 356b are inserted into the lumens 332a, 332b, respectively. The stylets 354, 356a, 356b can be formed from any material suitable for insertion into a patient including, for example, one or more metals (e.g., stainless steel, titanium, or the like), one or more alloys, one or more shape memory materials, one or more plastic resins, or the like.

The sheath 360 of the introducer 300 is suitable for disposing over at least a portion of the outer surface 312 of the needle assembly 310 and moving longitudinally relative to the needle assembly 310, as shown by directional arrow 362. In at least some embodiments, the sheath 360 is used to introduce a paddle lead into a target insertion location in proximity to a target stimulation location within the patient. In at least some embodiments, the sheath 360 is used to introduce the paddle lead when the sheath 360 is not disposed over the needle assembly 310.

Figure 4A:
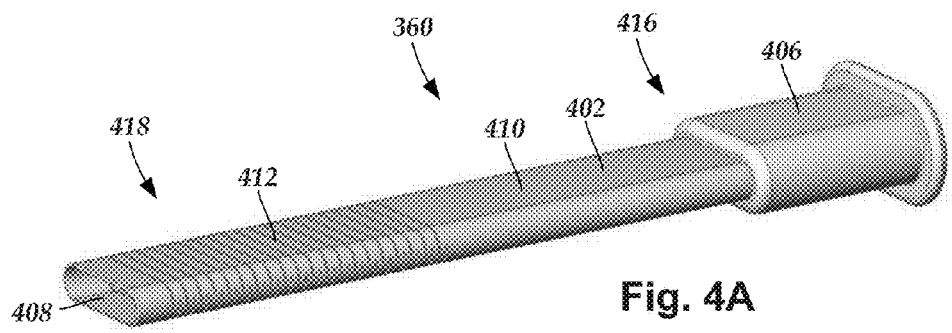
FIG. 4A is a schematic side perspective view of one embodiment of a sheath suitable for use with the multi-needle paddle lead introducer of FIG. 3A, according to the invention.
Figure 4B:
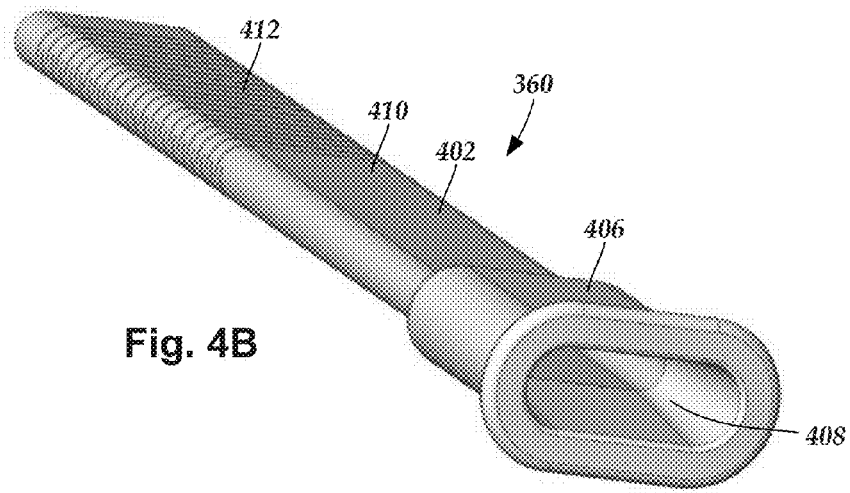
FIG. 4B is a schematic rear perspective view of one embodiment of the sheath of FIG. 4A, according to the invention.
Figure 4C:
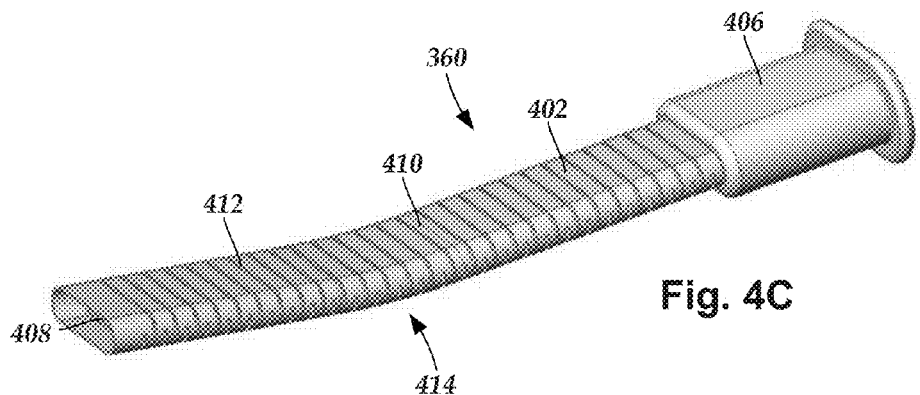
FIG. 4C is a schematic side perspective view of another embodiment of a sheath suitable for use with the multi-needle paddle lead introducer of FIG. 3A, according to the invention.

FIGS. 4A-4C illustrate, in perspective views, several different embodiments of the sheath 360. The sheath 360 includes a sheath body 402 and a handle 406 coupled to the sheath body 402. The sheath body 402 defines a lumen 408 suitable for receiving the needle assembly 310. The lumen is also suitable for receiving a paddle body (see e.g., 104 in FIGS. 1 and 1202 in FIG. 12). In at least some embodiments, the lumen is suitable for receiving the paddle body when the lumen 408 is not concurrently receiving the needle assembly 310. The sheath body 402 has an outer surface 410, a proximal end portion 416, a distal end portion 418, and a longitudinal length extending between the proximal end portion 416 and the distal end portion 418.

The sheath 360 can have any suitable profile along a plane traverse to the longitudinal length of the sheath body 402. In at least some embodiments, the sheath 360 has a profile along a plane traverse to the longitudinal length of the sheath body 402 that is the same as a profile of the needle assembly along a plane traverse to a longitudinal length of the needle assembly 310. In at least some embodiments, the sheath 360 has a profile along a plane traverse to the longitudinal length of the sheath body 402 that is the same as a profile of a paddle lead along a plane traverse to a longitudinal length of a paddle body of the paddle lead. In at least some embodiments, the sheath 360 has a non-round profile along a plane traverse to the longitudinal length of the sheath body 402. In at least some embodiments, the sheath 360 has profile that is rectangular or oval along a plane traverse to the longitudinal length of the sheath body 402. In at least some embodiments, the sheath 360 has a profile along a plane traverse to the longitudinal length of the sheath body 402 that includes two opposing semicircles coupled together by two opposing parallel lines, as shown in FIGS. 4A-4C.

In at least some embodiments, one or more cuts 412 are defined along on the outer surface 410 of the sheath body 402. The cuts 412 may extend around at least a portion of a circumference of the sheath 360. In other words, the cuts 412 may extend along at least a portion of an axis that is traverse to the longitudinal length of the needle assembly 310 when the sheath 360 is disposed on the needle assembly 310. In at least some embodiments, the one or more cuts 412 each extend around at least half of the circumference of the sheath 360.

The cuts may be disposed along all, or only a portion, of the longitudinal length of the sheath body. In FIGS. 4A-4B, the cuts 412 are defined exclusively along the distal end portion 418 of the sheath body 402. In FIG. 4C, the cuts 412 are defined along the entire longitudinal length of the sheath body 402. The embodiment of the sheath 360 shown in FIG. 4C may be especially useful in the embodiments of the introducer discussed below, with reference to FIGS. 15A-17.

The cuts 412 may provide flexibility to the distal end portion 418 of the sheath 360. For example, the cuts 412 may allow sheath 360 to slide smoothly along the longitudinal length of the needle assembly 310 when, for example, one or more portions of the needle assembly 310 are bent while inserted into the patient.

The cuts 412 can be formed using one or more suitable methods such as laser cutting, or the like. In at least some embodiments (see e.g., FIG. 4C), the sheath 360 includes a bend 414 formed along its longitudinal length, which may facilitate sliding of the sheath 360 along the needle assembly. In at least some embodiments, the bend 414 is permanently formed along the sheath 360. As mentioned above, the embodiment of the sheath 360 (with the bend 414) shown in FIG. 4C may be especially useful in the embodiments of the introducer discussed below, with reference to FIGS. 15A-17, which include a bend (1528 in FIG. 15A) formed along the one or more primary needles.

Defining cuts 412 in the sheath 360 enables the sheath 360 to be formed from one or more rigid materials (e.g., metal or high-durometer plastic, or the like) so that the sheath 360 does not kink or collapse during insertion and has a wall thickness that is thin, to reduce the amount of insertion force needed to insert the sheath 360 into patient tissue. In at least some embodiments, the sheath functions as a surgical retractor to spread tissue and bone (vertebrae) atraumatically to enable smooth, easy insertion of the paddle lead into the target insertion location.

In at least some embodiments, the bend 414 is formed along the distal end portion 418 of the sheath body 402. The bend 414 may thus provide flexibility to the sheath body 402, thereby facilitating advancement of the sheath 360 relative to the needle assembly 310. The bend 414 may facilitate insertion of the distal end portion 418 of the sheath 360 into the target insertion location.

In at least some embodiments, the handle 406 is coupled to the proximal end portion 416 of the sheath body 402. In at least some embodiments, the lumen 408 extends through the handle 406, as shown in FIG. 4B. The handle 406 may taper outwardly from the proximal end portion 416 of the sheath body 402. Such a design may facilitate insertion of the paddle lead into the lumen 408 of the sheath body 402. The handle 406 may be either temporarily or permanently coupled to the sheath body 402. The handle 406 may be coupled to the sheath body 402 by interference fit, gluing, welding, snap-fitting, or the like or combinations thereof.

Figure 5:
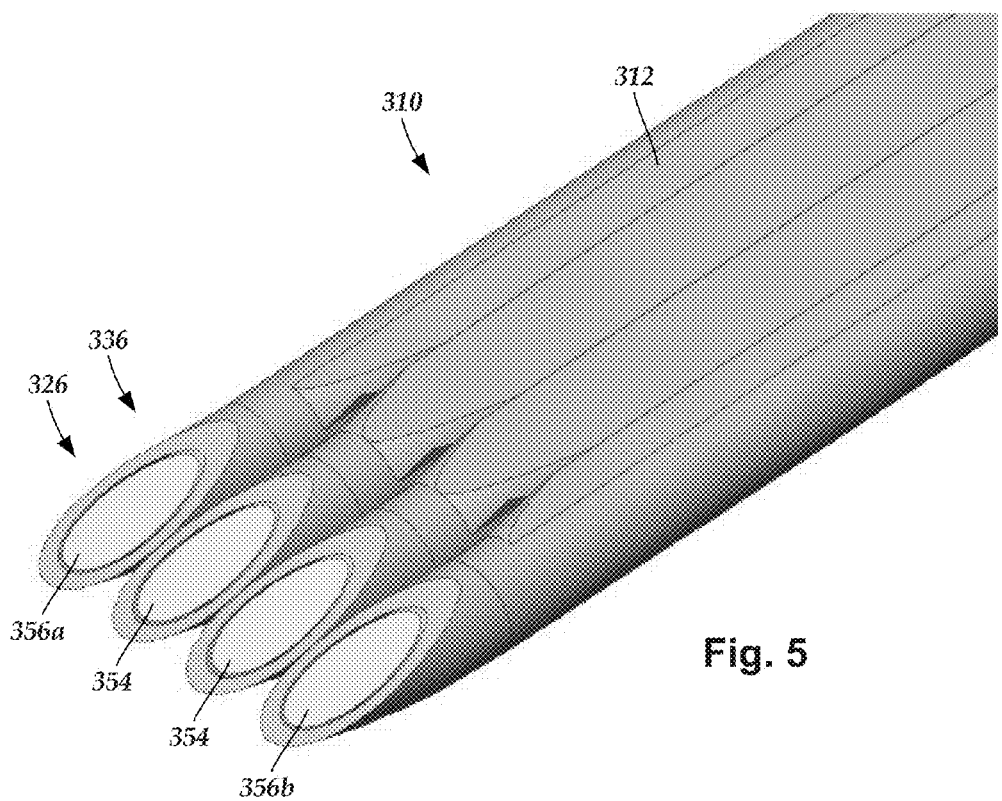
FIG. 5 is a schematic perspective, close-up view of one embodiment of a distal end portion of the needle assembly of FIG. 3B, the needle assembly having a flat major surface extending along at least a portion of the length of the needle assembly, according to the invention.

FIG. 5 is a close-up view of one embodiment of the distal end portion 316 of the needle assembly 310. In FIG. 5, the stylets 354, 356a, 356b are shown inserted into the lumens of the needles of the needle assembly 310. In at least some embodiments, the outer surface 312 of the needle assembly 310 includes opposing flat surfaces. In at least some embodiments, the outer surface 312 is flat along a plane transverse to the longitudinal length of the needle assembly 310. In at least some embodiments, the needle assembly 310 has a profile along a plane traverse to the longitudinal length of the sheath body 402 that includes two opposing semicircles coupled together by the two opposing parallel lines, as shown in FIG. 5. In at least some embodiments, the transverse cross-sectional shape of the needle assembly 310 is the same, or similar to, a transverse cross-sectional shape of lumen 408 of the sheath 360. In at least some embodiments, the transverse cross-sectional shape of the needle assembly 310 is the same, or similar to, a transverse cross-sectional shape of the paddle body.

Figure 6:
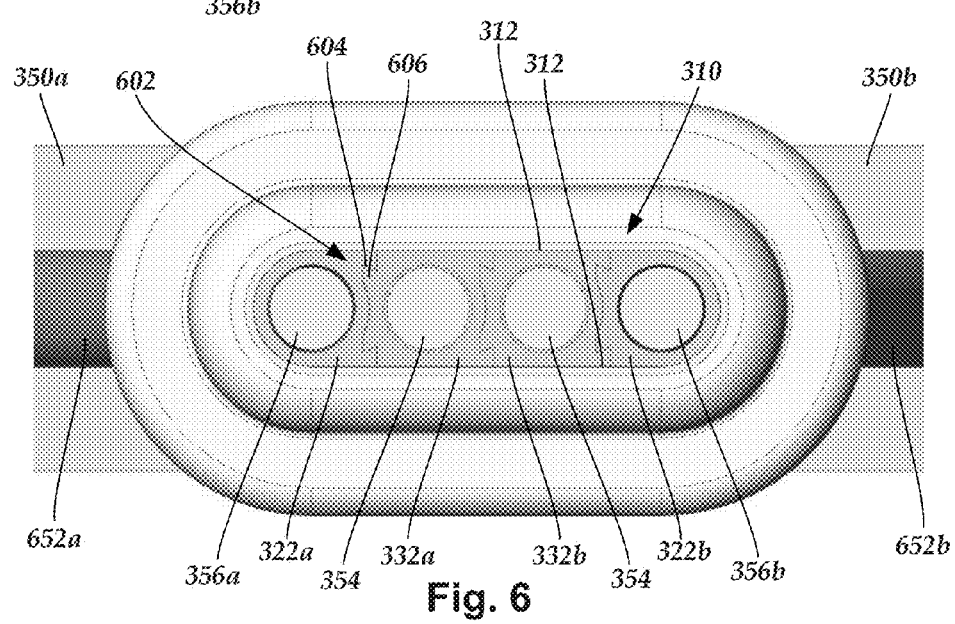
FIG. 6 is a schematic transverse cross-sectional view of one embodiment of the primary needles, secondary needles, hub assembly, and sheath of the multi-needle paddle lead introducer of FIG. 3B, the primary needles interconnected to the secondary needles via an interlocking connection formed between the primary and secondary needles, as well as between the multiple primary needles, according to the invention.

Turning to FIG. 6, in at least some embodiments at least one of the needles of the needle assembly forms an interlocking connection with at least one adjacent needle of the needle assembly. In at least some embodiments, the interlocking connection forms the needle assembly into a solid structure between the multiple needles. In at least some embodiments each of the needles of the needle assembly 310 (and the one or more interlocking connections between the needles) collectively form a solid structure that prevents tissue from being caught between individual needles of the needle assembly during insertion of the needle assembly into the patient.

FIG. 6 illustrates, in schematic transverse cross-sectional view, one embodiment of the needle assembly 310, the hub assembly 340, and the sheath 360 of the introducer. As shown, adjacent needles of the needle assembly 310 can, optionally, couple to one another along at least a portion of the longitudinal length of the needle assembly 310, via one or more interlocking connections.

FIG. 6 shows interlocking connections, such as interlocking connection 602, disposed between adjacent needles (primary-primary, primary-secondary, or secondary-secondary) of the needle assembly. The interlocking connections can be used to maintain the needle assembly 310 as a single structure with the needles coupled to one another in the side-by-side configuration. Additionally, the interlocking connection may facilitate movement of the one or more secondary needles relative to the one or more primary needles. The interlocking connections may prevent undesirable divergence of the needles during insertion. Needle divergence may potentially cause tissue to bunch up between the needles and prevent the sheath from being insertable far enough into the patient to enable lead insertion.

The interlocking connections can extend along all, or a portion, of the longitudinal length of the needle assembly. Any suitable number of interlocking connections can be disposed between particular adjacent needles including, for example, one, two, three, four, or more interlocking connections.

The interlocking connections can be formed in any suitable way for maintaining connection of the needles along the length of the needle assembly. In FIG. 6, the interlocking connections 602 are shown formed by coupling a groove 604 defined along a first of two adjacent, interconnected needles with an elongated projection 606 extending along a second of the two adjacent, interconnected needles.

FIG. 6 also illustrates the tabs 350a, 350b extending from the primary hub 342, as well as slots 652a, 652b that are defined in the tabs 350a, 350b, respectively, and that receive the secondary needles 330a, 330b, respectively. In at least some embodiments, the slots 652a, 652b have widths greater than the diameters of the secondary needles 330a, 330b, respectively, but less than the width of the secondary needle hubs 356a, 356b, respectively. Therefore, in at least some embodiments the slots 652a, 652b prevent undesired distal advancement of the secondary needle hubs 356a, 356b beyond a desired location.

Figure 7:
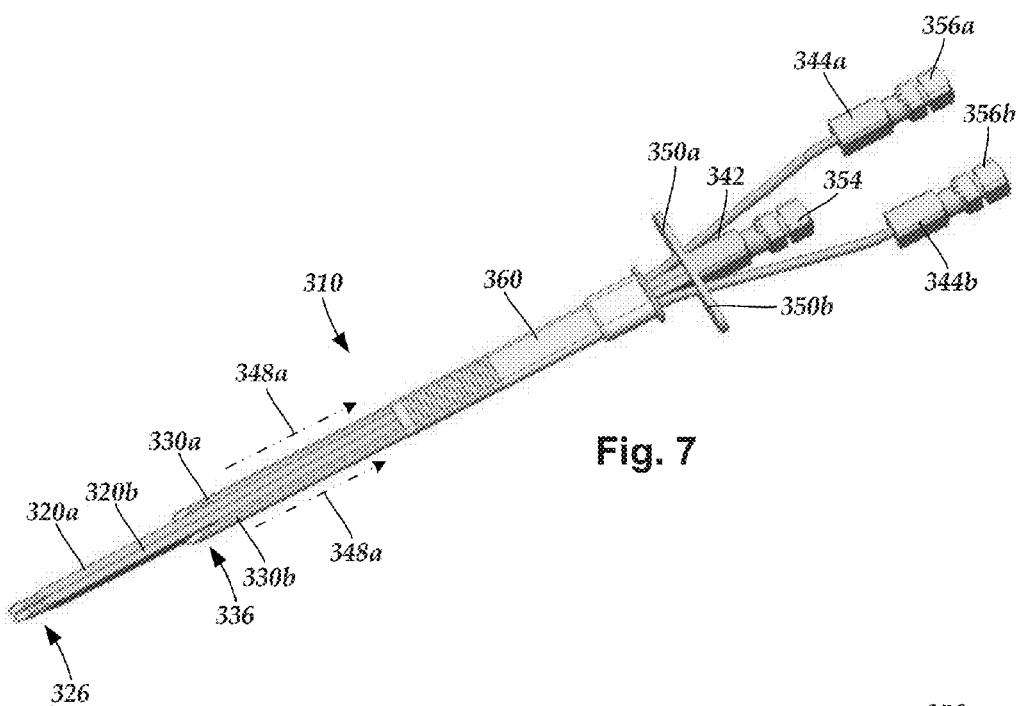
FIG. 7 is a schematic perspective view of one embodiment of the primary needles, secondary needles, hub assembly, and sheath of the multi-needle paddle lead introducer of FIG. 3B with the secondary needles retracted relative to the primary needles such that distal tips of the secondary needles are proximal to distal tips of the primary needles, according to the invention.

FIGS. 7-12 illustrate exemplary steps for one narrow embodiment of using the introducer to implant a paddle lead into a patient. FIG. 7 illustrates, in schematic perspective view, one embodiment of the introducer with the secondary needles 330a, 330b retracted relative to the primary needles 320a, 320b such that the distal tips 336 of the secondary needles are proximal to the distal tips 326 of the primary needles.

In at least some embodiments, the secondary needles 330a, 330b are retracted by pulling the needles 330a, 330b along a direction identified by directional arrows 348a. The retraction of the secondary needle 330 may be performed using the secondary-needle hubs 344a, 344b. In at least some embodiments, the needle assembly 310 is manufactured with the secondary needles 330a and 330b retracted relative to the primary needles 320a and 320b. In the retracted position, the distal tips 336b of the secondary needle 330a, 330b are positioned proximal to the distal tips 326 of the primary needles 320a, 320b.

In FIG. 7, stylets 354, 356a, and 356b are shown inserted into the needle lumens of the primary and secondary needles. In at least some embodiments, the stylets are inserted into the lumens of the needles prior to insertion of the needles into the patient. In other embodiments, the stylets are pre-installed (i.e., inserted during manufacture).

Figure 8:
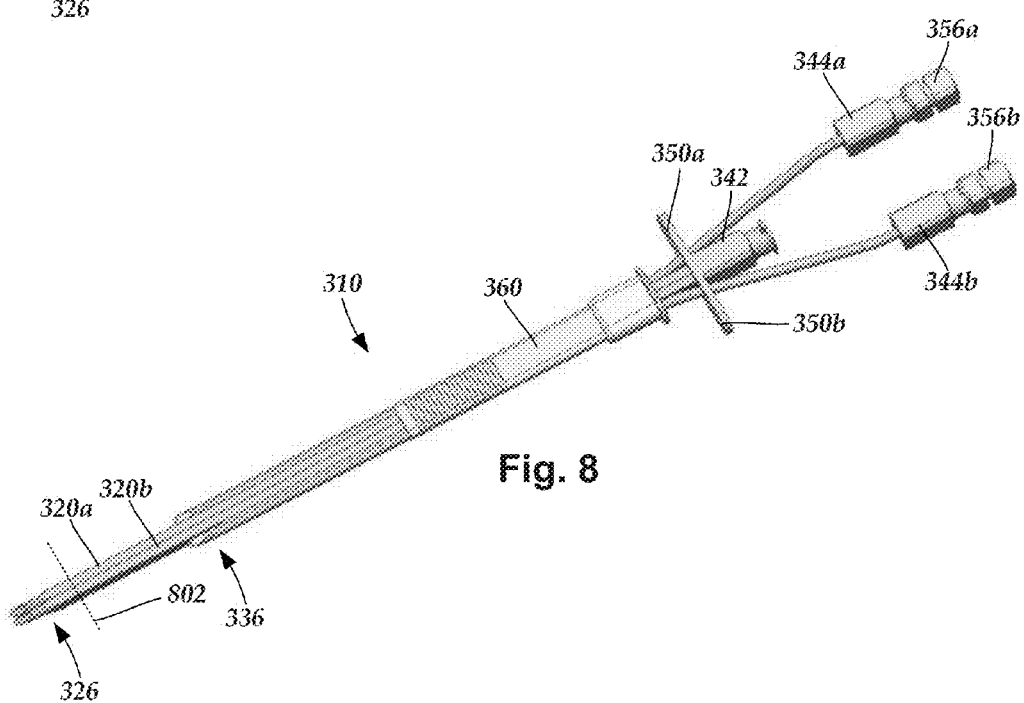
FIG. 8 is a schematic perspective view of one embodiment of the primary needles, secondary needles, hub assembly, and sheath of the multi-needle paddle lead introducer of FIG. 7 with distal tips of the primary needles inserted into a target insertion location within a patient and stylets removed from the primary needles in preparation for performing a loss-of-resistance test to confirm the location of the distal tips of the primary needles, according to the invention.

FIG. 8 illustrates, in schematic perspective view, one embodiment of the introducer with the primary needles 320a, 320b advanced through patient tissue. In FIG. 8, the distal tips 326 of the primary needles are shown disposed at a target insertion location 802. In at least some embodiments, the target insertion location 802 is a region in proximity to the target stimulation location. When, for example, the target stimulation location is the epidural space, the target insertion location may be a location in, or in proximity to, the epidural space. In at least some embodiments, the target insertion location is a location that is proximal or distal (with respect to the patient) to the target stimulation location within the epidural space.

FIG. 8 also shows the stylets 354 removed from the primary needles. Once the primary needles 320a and 320b are positioned within the target insertion location, the stylets 354 (as shown in FIG. 7) may be removed. In at least some embodiments, a loss-of-resistance test is performed subsequent to removal of the stylets to confirm the location of the distal tips 326 of the primary needles 320a, 320b (e.g., to determine whether or not the distal tips 326 of the primary needles 320a, 320b are disposed in the epidural space). Other techniques may be used for determining the location of the distal tips 326 within the patient instead of, or in addition to, performing a loss-of-resistance test including, for example, one or more modalities of medical imaging.

Figure 9:
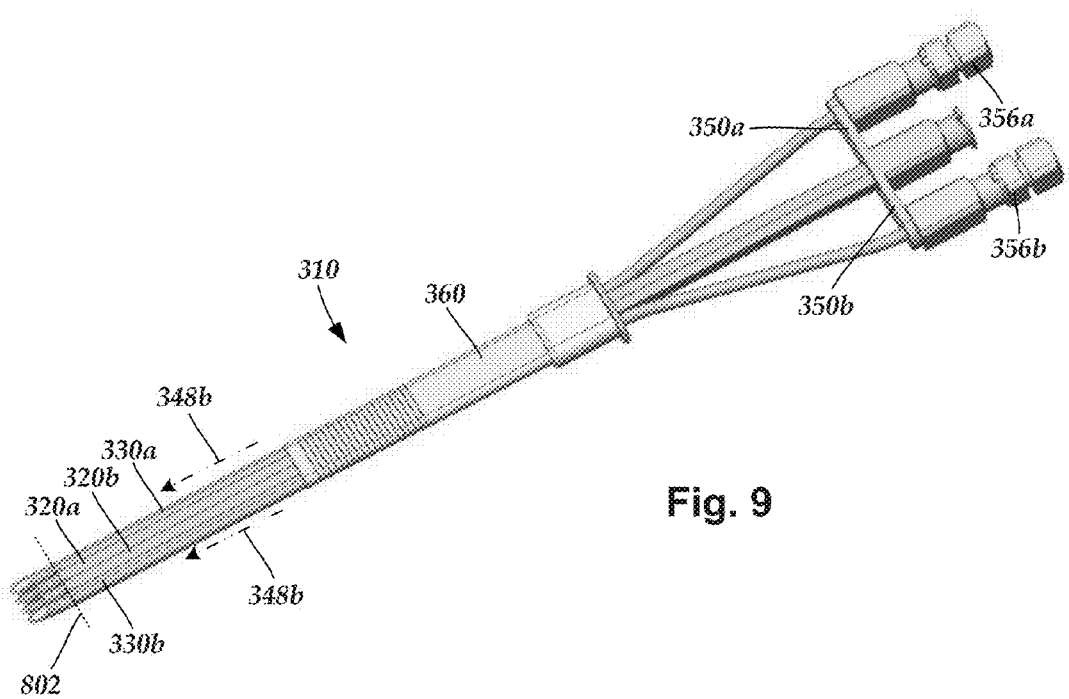
FIG. 9 is a schematic perspective view of one embodiment of the primary needles, secondary needles, hub assembly, and sheath of the multi-needle paddle lead introducer of FIG. 8 with the secondary needles advanced relative to the primary needles so that the distal tips of the secondary needles are inserted into the target insertion location along with the distal tips of the primary needles, advancement of the secondary needles limited by slots of tabs that are disposed on the hub assembly and through which the secondary needles extend, according to the invention.

FIG. 9 illustrates, in schematic perspective view, one embodiment of the introducer with the secondary needles 330 advanced relative to the primary needles 320a and 320b, and with the stylets removed from the primary lumens. In at least some embodiments, the secondary needles 330 are not advanced until after the location of the distal tips 326 of the primary needles at the target insertion location 802 is confirmed.

The secondary needles 330 may be advanced distally, as shown by directional arrow 348b, such that the distal tips 336 of the secondary needles 330 are inserted into the target insertion location adjacent the distal tips 326 of the primary needles 320a and 320b, thereby enlarging the incision made through patient tissue by the primary needles. In embodiments with multiple secondary needles, the secondary needles can be advanced either sequentially or concurrently. In at least some embodiments, the distal advancement of secondary needles relative to the primary needles are limited by the slots of the tabs of the hub assembly 340.

In embodiments where stylets are inserted into the secondary needles prior to insertion, the stylets are removed upon entry of the distal tips 336 of the secondary needles into the target insertion location 802. Optionally, the location(s) of the distal tip(s) 336 of the secondary needles may be verified (e.g., via a loss-of-resistance test, imaging, or the like) subsequent to insertion of the second needles into the target insertion location. In preferred embodiments, the location of one or more needles of the needle assembly is verified prior to insertion of the sheath into the target insertion location.

Figure 10:
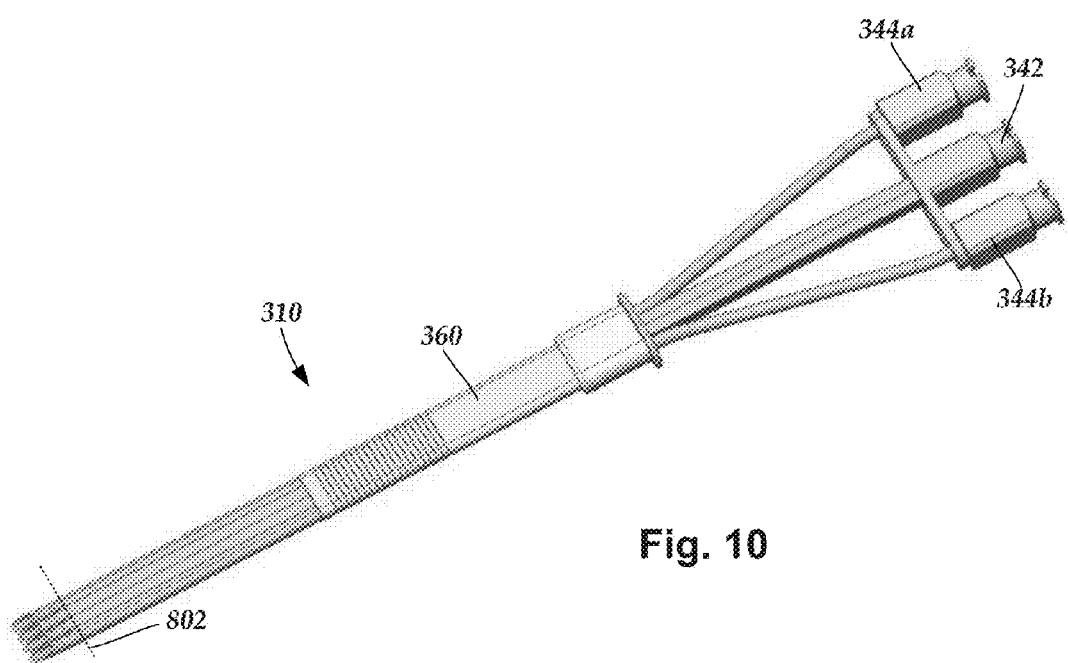
FIG. 10 is a schematic perspective view of one embodiment of the primary needles, secondary needles, hub assembly, and sheath of the multi-needle paddle lead introducer of FIG. 9 with stylets removed from the secondary needles, according to the invention.

FIG. 10 illustrates, in schematic perspective view, one embodiment of the introducer with the distal tips 326, 336 of all of the needles of the needle assembly 310 disposed at the target insertion location 802 and with the stylets removed from each of the needles of the needle assembly.

Figure 11:
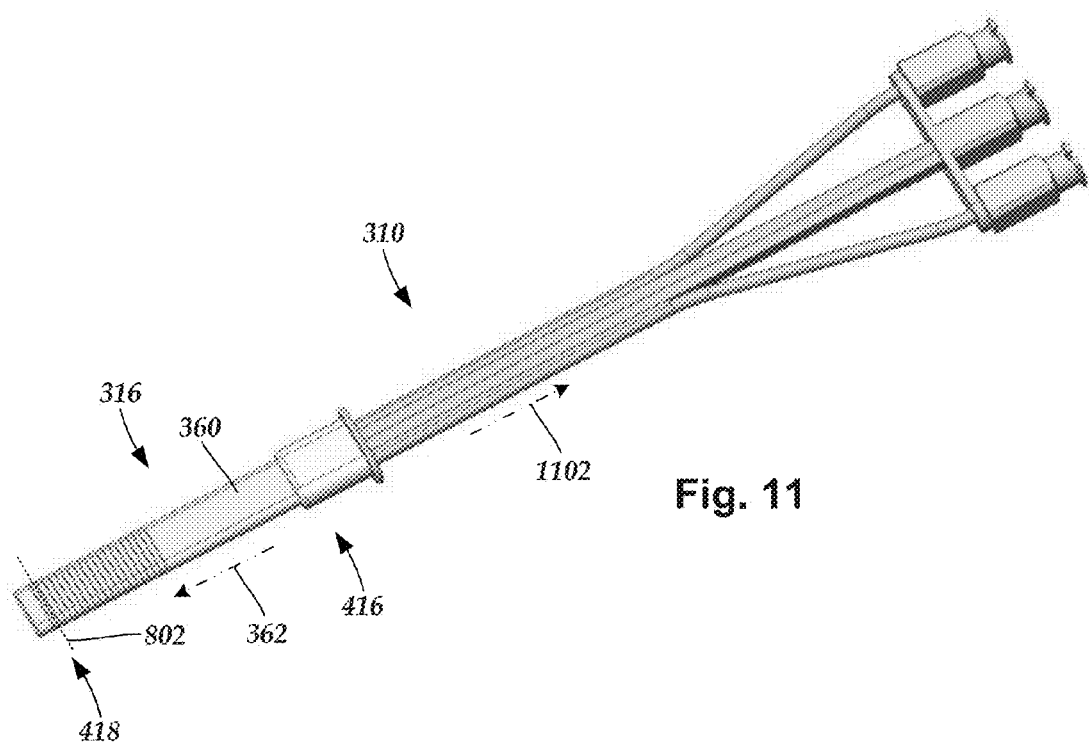
FIG. 11 is a schematic perspective view of one embodiment of the primary needles, secondary needles, hub assembly, and sheath of the multi-needle paddle lead introducer of FIG. 10 with the sheath advanced distally along an outer surface of the primary and secondary needles such that a portion of the sheath is inserted into the target insertion location along with the distal tips of the primary and secondary needles, according to the invention.

FIG. 11 illustrates, in schematic perspective view, one embodiment of the introducer with the sheath 360 advanced distally along the needle assembly 310, as shown by directional arrow 362. In FIG. 11, the sheath 360 is shown advanced distally along the needle assembly 310 until a portion of the sheath 360 reaches the target insertion location 802.

Once the distal end portion of the sheath 360 is located at the target insertion location, the needle assembly 310 (and attached hub assembly 340) can be removed from the patient leaving the sheath 360 partially disposed in the target insertion location 802. In at least some embodiments, the proximal end portion of the sheath 360 extends outwardly from the patient when the distal end portion of the sheath 360 is disposed at the target insertion location 802. The needle assembly 310 is typically removed from the patient along the proximal end portion of the sheath 360 in a direction shown by directional arrow 1102.

Figure 12:
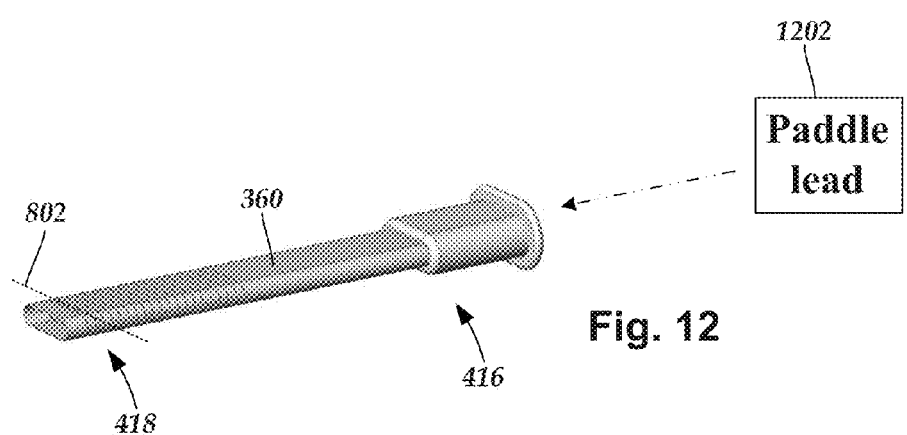
FIG. 12 is a schematic perspective view of one embodiment of a paddle lead configured for insertion into the sheath of FIG. 11 after the sheath is partially inserted into the target insertion location and the primary needles, secondary needles, and hub assembly of the multi-needle paddle lead introducer of FIG. 11 are removed from the sheath, according to the invention.

FIG. 12 illustrates, in perspective view, one embodiment of a paddle lead 1202 suitable for insertion into the sheath 360 after the sheath 360 is partially inserted into the target insertion location. The paddle lead is advanced through the lumen (408 of FIGS. 4A-4C) of the sheath 360 to reach the target insertion location 802 within the patient. Once the paddle body of the paddle lead 1202 is disposed at the target insertion location 802, the sheath 360 can be removed from the patient, leaving the paddle body of the paddle lead disposed at the target insertion location. Once the paddle body of the paddle lead 1202 is disposed at the target insertion location 802, the paddle body can be positioned at the nearby target stimulation location, either before or after removal of the sheath 360 from the patient.

Figure 13:
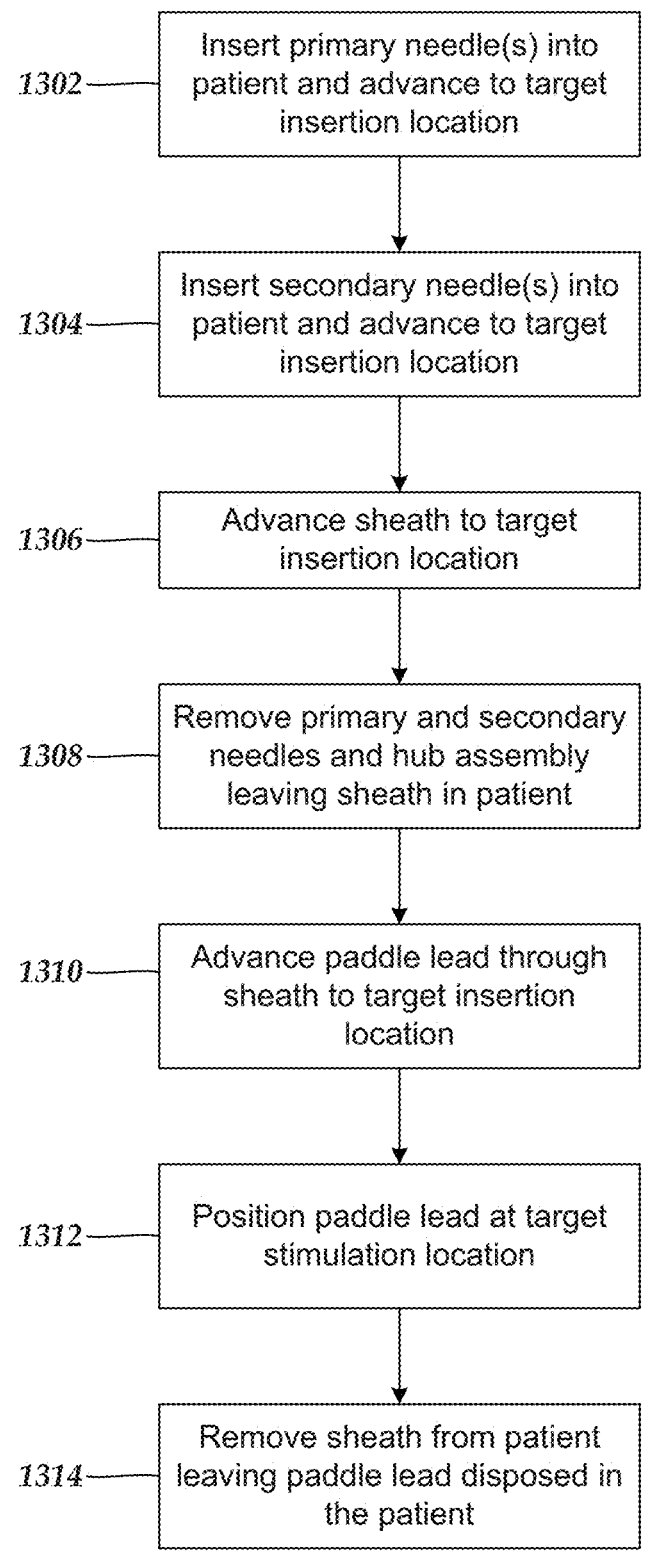
FIG. 13 is one embodiment of a flow diagram illustrating steps for introducing a paddle lead into a patient using a multi-needle paddle lead introducer, according to the invention.

FIG. 13 is a flow diagram illustrating one embodiment for implanting a paddle lead into a patient using the introducer 300. In step 1302, the primary needles 320a, 320b are inserted into a patient and advanced to a target insertion location. In step 1304, the secondary needles 330a, 330b are inserted into the patient and advanced to the to the target insertion location. In step 1306, the sheath 360 is advanced to the target insertion location. In step 1308, the needle assembly and the hub assembly 340 are removed from the patient leaving the sheath 360 at the target insertion location. In step 1310, the paddle lead 1202 is advanced, via the sheath, to the target insertion location. In step 1312, the paddle lead 1202 is positioned at the target stimulation location. In step 1314, the sheath is removed from the patient leaving the paddle lead 1202 disposed in the patient. It will be understood that the paddle lead 1202 may be positioned at the target stimulation location either before or after the sheath is removed from the patient.

Figure 14:
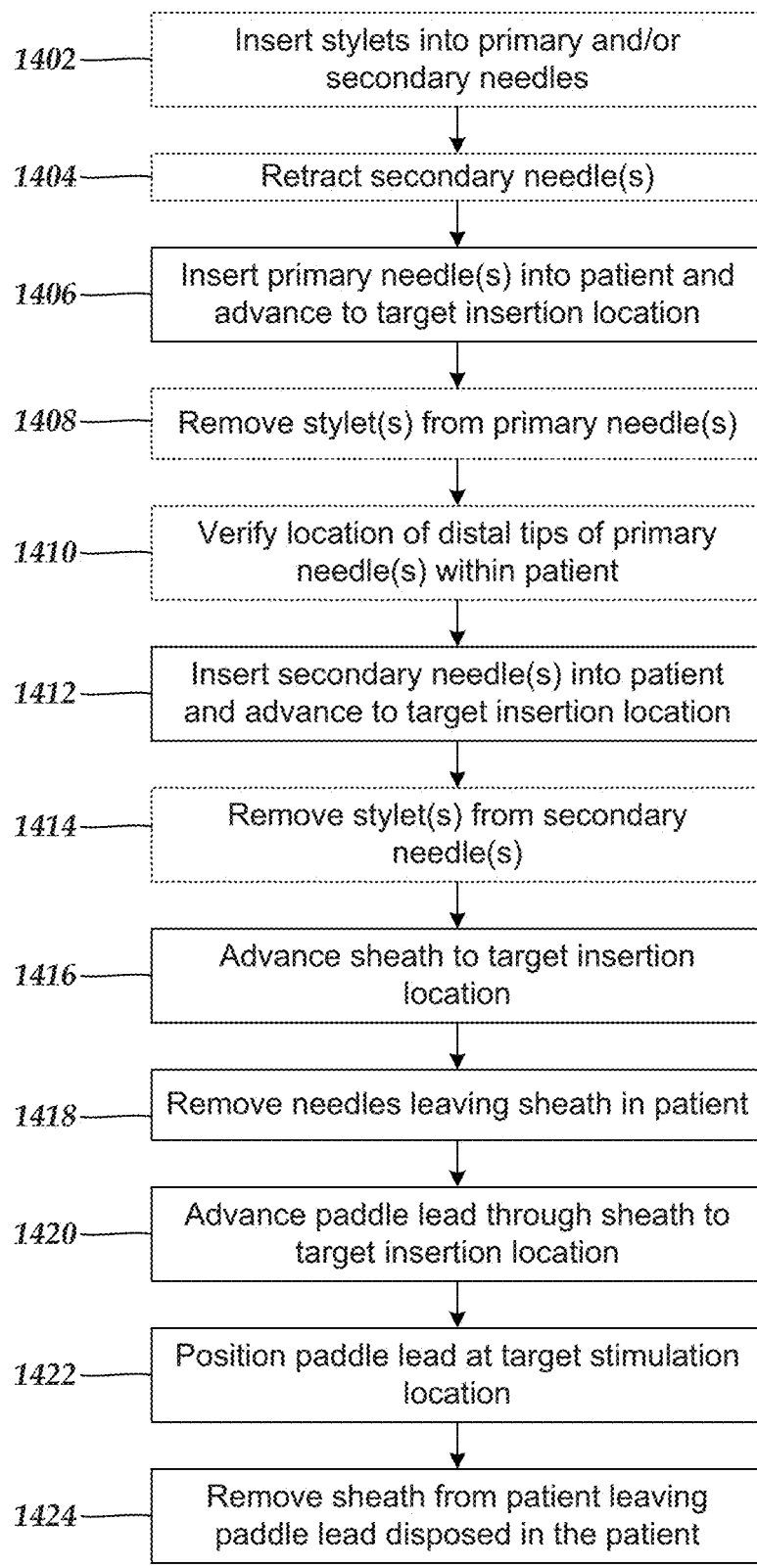
FIG. 14 is another embodiment of a flow diagram illustrating steps for introducing a paddle lead into a patient using a multi-needle paddle lead introducer, according to the invention.

FIG. 14 is a flow diagram illustrating another embodiment for implanting a paddle lead into a patient using the introducer 300. Optionally, in step 1402 stylets are inserted into at least one of the needles of the needle assembly 310. Optionally, in step 1404 the secondary needles 330 are retracted proximally relative to the primary needles. In step 1406, the primary needles 320a, 320b are inserted into a patient and advanced to a target insertion location. In step 1304, the secondary needles 330a, 330b are inserted into the patient and advanced to the target insertion location. Optionally, in step 1408 the stylets are removed from the primary needles 320a, 320b. Optionally, in step 1410 the location of the distal tips 326 of the primary needles is verified. In step 1412, the secondary needles 330a, 330b are inserted into the patient and advanced to the to the target insertion location. Optionally, in step 1414, the stylets are removed from the secondary needles 330a, 330b. In step 1416, the sheath 360 is advanced to the target insertion location. In step 1418, the needle assembly and the hub assembly 340 are removed from the patient leaving the sheath 360 at the target insertion location. In step 1420, a paddle lead 1202 is advanced, via the sheath, to the target insertion location. In step 1422, the paddle lead is positioned at the target stimulation location. In step 1424, the sheath is removed from the patient leaving the paddle lead 1202 disposed in the patient. It will be understood that the paddle lead 1202 may be positioned at the target stimulation location either before or after the sheath is removed from the patient.

Turning to FIGS. 15A-15B, in at least some embodiments the primary needle(s) include(s) a permanent bend for facilitating advancement of the introducer within the patient. FIG. 15A illustrates, in schematic perspective view, another embodiment of an introducer 1500. The introducer 1500 includes a needle assembly 1510, a hub assembly 1540, and a sheath 1560.

The needle assembly 1510 includes one or more primary needles. In FIG. 15A (and in other figures), the needle assembly 1510 includes primary needles 1520a, 1520b having distal end portions 1524 with distal tips 1526. The needle assembly 1510 further includes one or more secondary needles. In FIG. 15A (and in other figures), the needle assembly 1510 includes secondary needles 1530a, 1530b having distal end portions 1534 with distal tips 1536. The needles of the needle assembly 1510 are similar in form and function to that of the needles of the needle assembly 310 of FIGS. 3A-12.

Turning briefly to FIG. 15B, a permanent bend 1528 is shown formed along the distal end portion 1524 of the primary needle 1520b of the needle assembly 1510. In at least some embodiments, the bend 1528 is formed along each of the primary needles of the needle assembly 1510. The bend 1528 may facilitate advancement of the primary needles through patient tissue. The bend 1528 may, for example, facilitate advancement of the primary needles 1520a, 1520b into the target insertion location (e.g., the epidural space).

In at least some embodiments, the bend 1528 has an angle 1529 that is at least 5°, 10°, 15°, or 20°. In at least some embodiments, the bend 1528 has an angle 1529 that is no greater than 20°, 15°, or 10°. In at least some embodiments, the bend 1528 has an angle 1529 that is at least 5° and no greater than 20°. In at least some embodiments, the bend 1528 has an angle 1529 that is at least 10° and no greater than 15°.

Turning back to FIG. 15A, in at least some embodiments the secondary needles 1530a, 1530b are configured to slide along the bend 1528 relative to the primary needles 1520a, 1520b. In at least some embodiments, the secondary needles 1530a, 1530b define multiple cuts 1538 formed along a distal end portion 1534 of the secondary needles 1530a, 1530b. The cuts 1538 enable the secondary needles 1530a, 1530b to advance along the bend 1528 of the primary needle 1520a, 1520b. In at least some embodiments, the cuts 1538 extend circumferentially around at least half of a circumference of the secondary needles secondary needles 1530a, 1530b. In at least some embodiments, a thin-walled flexible inner tube may be incorporated into the secondary needles in order to maintain a fluid/gas seal between the Luer hubs and the distal tips of the secondary needles to enable performance of the loss-of-resistance technique.

A proximal end portion of the needle assembly 1510 is coupled to the hub assembly 1540. The hub assembly 1510 includes a primary needle hub 1542 coupled to the proximal end portion of the primary needles 1520a, 1520b and secondary needle hubs 1544a, 1544b coupled to the proximal end portions of the secondary needles 1530a, 1530b, respectively. The hub assembly 1540 is similar in form and function to that of the hub assembly 340 of FIGS. 3A-12.

In at least some embodiments, the primary needle hub 1542 includes a connection mechanism suitable for coupling the secondary needle hubs 1544a, 1544b to the primary needle hub 1542. In FIG. 15A (and in other figures), the primary needle hub 1542 includes a first tab 1550a and a second tab 1550b extending outwards from opposing side of the primary needle hub 1542. Each tab 1550a, 1550b defines a slot 1552a, 1552b, respectively, suitable for receiving the secondary needles 1530a, 1530b, respectively.

In at least some embodiments, the slots 1552a, 1552b are sized such that the secondary needles 1530a, 1530b, respectfully, can move relative to the primary needle hub 1542 along the longitudinal length of the needle assembly 1510. In at least some embodiments, the slots 1552a, 1552b are sized such that the secondary needle hubs 1544a, 1544b are prevented from passing through the slots 1552a, 1552b. In which case, the slots 1552a, 1552b control the distance along which the secondary needles 1530a, 1530b, respectfully, can move distally relative to the primary needle hub 1542 along the longitudinal length of the needle assembly 1510.

In at least some embodiments, at least one of the needle hubs 1542, 1544a, 1544b includes a proximal female Luer hub assembly suitable for receiving a Luer tip syringe. In FIG. 15A, stylets 1554, 1556a, and 1556b are shown inserted into the needles.

The sheath 1560 is suitable for disposing over at least a portion of the needle assembly 1510 and sliding longitudinally relative to the needle assembly 1510. The sheath 560 is used to introduce a paddle lead into the target insertion location. The sheath 1560 is similar in form and function to that of sheath 360 of FIGS. 3A-12.

Figure 16:
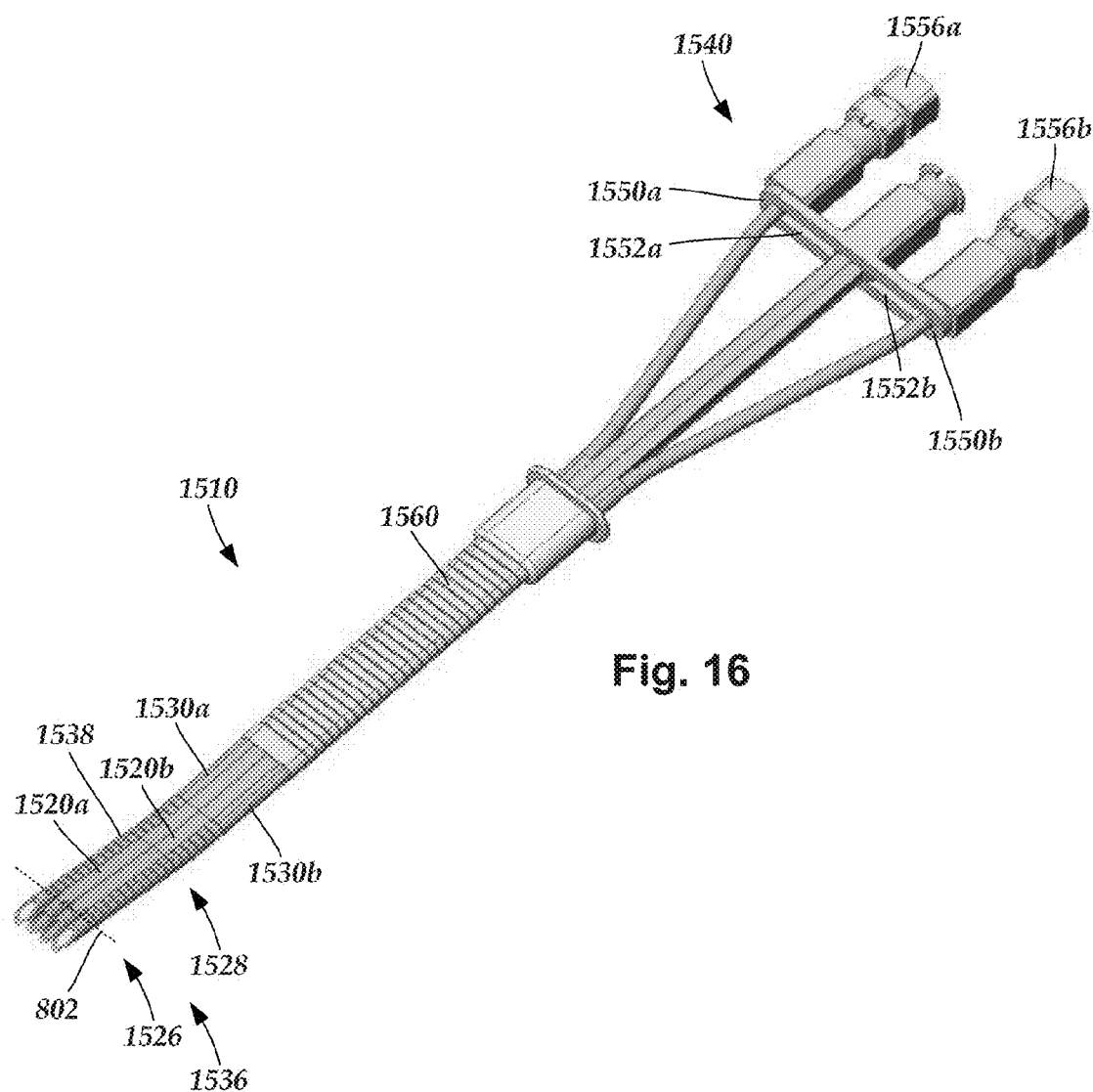
FIG. 16 is a schematic perspective view of one embodiment of the primary needles, secondary needles, and sheath of the multi-needle paddle lead introducer of FIG. 15 with distal tips of the primary needles advanced into a target insertion location, and with the secondary needles advanced distally relative to the primary needles such that distal tips of the secondary needles are also inserted into the target insertion location, according to the invention.

FIG. 16 illustrates, in perspective view, one embodiment of the needle assembly 1510, the hub assembly 1540, and the sheath 1560 of the introducer. The distal tips 1526 of the primary needles 1520a and 1520b, as well as the distal tips 1536 of the secondary needles 1530a, 1530b are advanced into the target insertion location 802. The slots 1552a, 1552b of the tabs 1550a, 1550b, respectively, prevent the distal tips 1536 of the secondary needles from extending proximally beyond the distal tips 1526 of the primary needles. The cuts 1538 of the secondary needles enable the secondary needles to advance along the bend 1528 of the primary needles. In FIG. 16, stylets 1556 are shown disposed in the secondary needles 1530a, 1530b.

Figure 17:
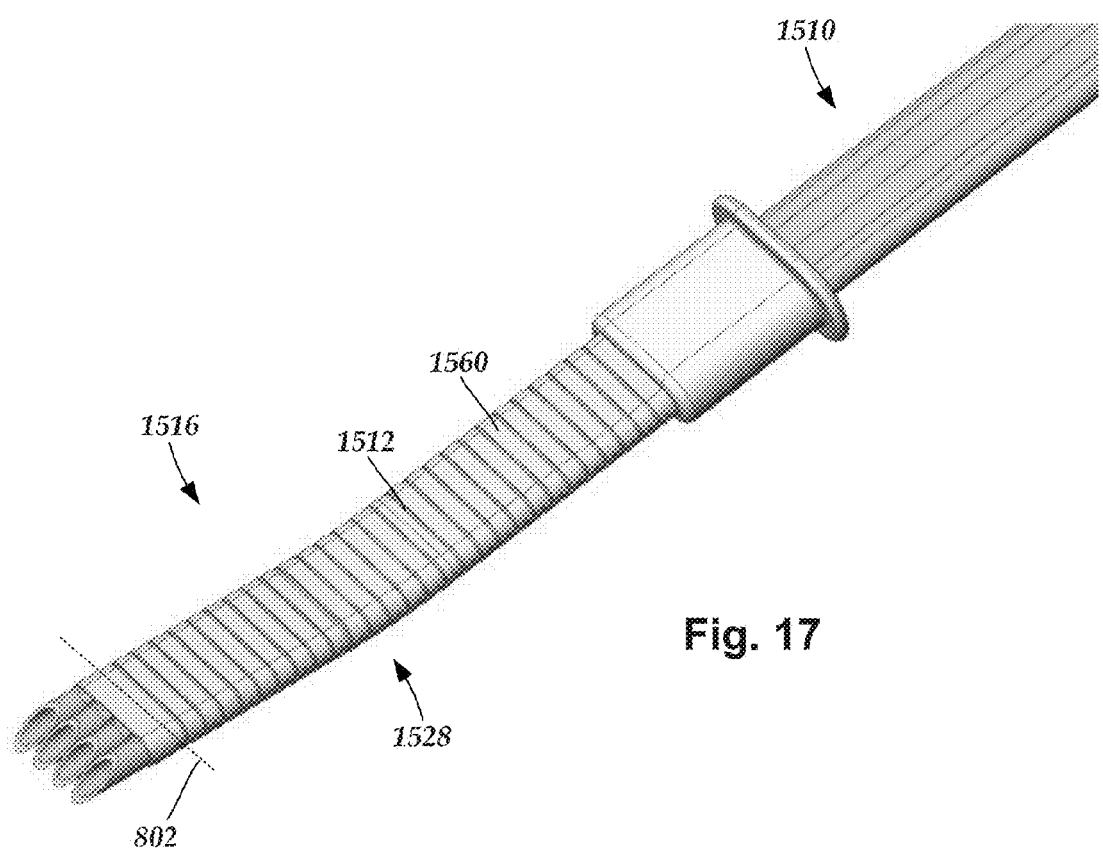
FIG. 17 is a schematic perspective view of one embodiment of the primary needles, secondary needles, and sheath of the multi-needle paddle lead introducer of FIG. 16 with the sheath advanced distally relative to the primary and secondary needles such that the sheath is partially inserted into the target insertion location along with distal tips of the primary and secondary needles, according to the invention.

FIG. 17 illustrates, in perspective view, one embodiment of distal end portion 1516 of the needle assembly 1510 with the sheath 1560 advanced distally relative to the needle assembly 1510 and partially inserted into the target insertion location 802. One or more cuts 1560 disposed along the sheath 1560 enable the sheath 1560 to advance along the bend 1528 of the primary needles.

Figure 18:
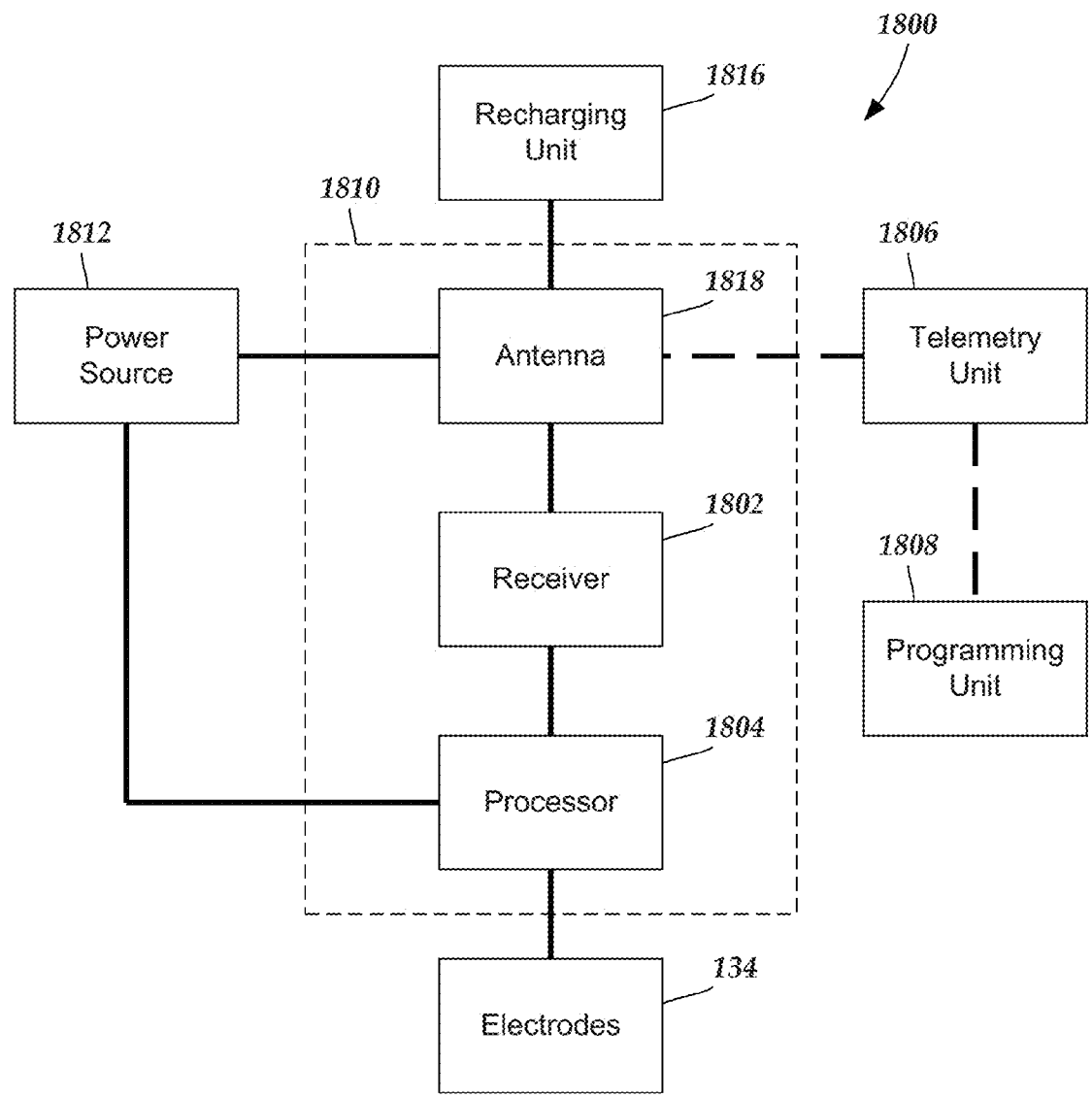
FIG. 18 is a schematic overview of one embodiment of components of a stimulation system, including an electronic subassembly disposed within a control module, according to the invention.

FIG. 18 is a schematic overview of one embodiment of components of an electrical stimulation system 1800 including an electronic subassembly 1810 disposed within a control module. It will be understood that the electrical stimulation system can include more, fewer, or different components and can have a variety of different configurations including those configurations disclosed in the stimulator references cited herein.

Some of the components (for example, a power source 1812, an antenna 1818, a receiver 1802, and a processor 1804) of the electrical stimulation system can be positioned on one or more circuit boards or similar carriers within a sealed housing of an implantable pulse generator, if desired. Any power source 1812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1818 or a secondary antenna. The external power source can be in a device that is mounted on the skin of the user or in a unit that is provided near the user on a permanent or periodic basis.

If the power source 1812 is a rechargeable battery, the battery may be recharged using the optional antenna 1818, if desired. Power can be provided to the battery for recharging by inductively coupling the battery through the antenna to a recharging unit 1816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1804 is generally included to control the timing and electrical characteristics of the electrical stimulation system. For example, the processor 1804 can, if desired, control one or more of the timing, frequency, strength, duration, and waveform of the pulses. In addition, the processor 1804 can select which electrodes can be used to provide stimulation, if desired. In some embodiments, the processor 1804 selects which electrode(s) are cathodes and which electrode(s) are anodes. In some embodiments, the processor 1804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1808 that, for example, allows modification of pulse characteristics. In the illustrated embodiment, the processor 1804 is coupled to a receiver 1802 which, in turn, is coupled to the optional antenna 1818. This allows the processor 1804 to receive instructions from an external source to, for example, direct the pulse characteristics and the selection of electrodes, if desired.

In one embodiment, the antenna 1818 is capable of receiving signals (e.g., RF signals) from an external telemetry unit 1806 which is programmed by the programming unit 1808. The programming unit 1808 can be external to, or part of, the telemetry unit 1806. The telemetry unit 1806 can be a device that is worn on the skin of the user or can be carried by the user and can have a form similar to a pager, cellular phone, or remote control, if desired. As another alternative, the telemetry unit 1806 may not be worn or carried by the user but may only be available at a home station or at a clinician's office. The programming unit 1808 can be any unit that can provide information to the telemetry unit 1806 for transmission to the electrical stimulation system 1800. The programming unit 1808 can be part of the telemetry unit 1806 or can provide signals or information to the telemetry unit 1806 via a wireless or wired connection. One example of a suitable programming unit is a computer operated by the user or clinician to send signals to the telemetry unit 1806.

The signals sent to the processor 1804 via the antenna 1818 and the receiver 1802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1800 to cease operation, to start operation, to start charging the battery, or to stop charging the battery. In other embodiments, the stimulation system does not include the antenna 1818 or receiver 1802 and the processor 1804 operates as programmed.

Optionally, the electrical stimulation system 1800 may include a transmitter (not shown) coupled to the processor 1804 and the antenna 1818 for transmitting signals back to the telemetry unit 1806 or another unit capable of receiving the signals. For example, the electrical stimulation system 1800 may transmit signals indicating whether the electrical stimulation system 1800 is operating properly or not or indicating when the battery needs to be charged or the level of charge remaining in the battery. The processor 1804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A multi-needle paddle lead introducer comprising:
   a needle assembly having an outer surface and a longitudinal length, the needle assembly comprising
      at least one primary needle having an outer surface, a longitudinal length, a proximal end portion, a distal end portion, and a sharpened distal tip, the at least one primary needle comprising a lumen extending along the longitudinal length of the at least one primary needle; and
      at least one secondary needle coupled to the at least one primary needle along at least a portion of the longitudinal length of the needle assembly such that the at least one primary needle and the at least one secondary needle are arranged in a side-by-side configuration, the at least one secondary needle having an outer surface, a longitudinal length, a proximal end portion, a distal end portion, and a sharpened distal tip, the at least one secondary needle comprising a lumen extending along the longitudinal length of the at least one secondary needle, wherein the at least one secondary needle is configured and arranged to move relative to the at least one primary needle along the longitudinal length of the needle assembly;
   a hub assembly coupled to the needle assembly, the hub assembly comprising
      at least one primary needle hub coupled to the proximal end portion of the at least one primary needle, and
      at least one secondary needle hub coupled to the proximal end portion of the at least one secondary needle; and
   a sheath having an outer surface and a longitudinal length, the sheath configured and arranged for disposing over at least a portion of the outer surface of the needle assembly and for sliding along the longitudinal length of the needle assembly.

2. The multi-needle paddle lead introducer of claim 1, further comprising at least one tab extending outwardly from the at least one primary needle hub, the at least one tab defining a slot.

3. The multi-needle paddle lead introducer of claim 2, wherein the at least one secondary needle extends through the slot defined in the at least one tab.

4. The multi-needle paddle lead introducer of claim 3, wherein the slot defined in the at least one tab prevents the distal tip of the at least one secondary needle from extending distally beyond the distal tip of the at least one primary needle.

5. The multi-needle paddle lead introducer of claim 1, further comprising a bend of at least 5° permanently formed along the distal end portion of the at least one primary needle.

6. The multi-needle paddle lead introducer of claim 1, further comprising a plurality of cuts defined along the outer surface of the distal end portion of the at least one secondary needle, the plurality of cuts facilitating bending of the at least one secondary needle.

7. The multi-needle paddle lead introducer of claim 1, wherein the at least one secondary needle is coupled by an interlocking connection to the at least one primary needle.

8. The multi-needle paddle lead introducer of claim 7, wherein the interlocking connection forms a solid structure between the at least one primary needle and the at least one secondary needle, the solid structure preventing patient tissue from getting caught between the at least one primary needle and the at least one secondary needle during insertion of the needle assembly into a patient.

9. The multi-needle paddle lead introducer of claim 1, wherein the outer surface of the needle assembly comprises opposing flat surfaces.

10. The multi-needle paddle lead introducer of claim 1, wherein at least one of the lumen of the at least one primary needle or the lumen of the at least one secondary needle is configured and arranged to receive a stylet to prevent coring of patient tissue when the needle assembly is inserted into a patient.

11. The multi-needle paddle lead introducer of claim 1, further comprising a plurality of cuts defined along the outer surface of the sheath, the plurality of cuts facilitating bending of the sheath.

12. The multi-needle paddle lead introducer of claim 1, wherein the sheath has a non-round profile along a plane transverse to the longitudinal length of the sheath.

13. The multi-needle paddle lead introducer of claim 1, wherein the at least one secondary needle comprises two secondary needles flanking the at least one primary needle.

14. The multi-needle paddle lead introducer of claim 1, wherein the at least one primary needle comprises two primary needles coupled to one another along the entire longitudinal length of the needle assembly.

15. An insertion kit comprising:
   the multi-needle paddle lead introducer of claim 1; and
   a paddle lead configured and arranged for insertion into a patient using the lead introducer, the paddle lead comprising:
      at least one lead body having a distal end portion, a proximal end portion, and a longitudinal length,
      a paddle body attached to the distal end portion of the at least one lead body,
      a plurality of electrodes disposed along the paddle body,
      a plurality of terminals disposed along the proximal end portion of the at least one lead body, and a plurality of conductors electrically coupling the plurality of electrodes to the plurality of terminals.

16. An electrical stimulating system comprising:
the insertion kit of claim 15;
a control module coupleable to the paddle lead of the insertion kit, the control module comprising
a housing, and
an electronic subassembly disposed in the housing; and
a connector for receiving the paddle lead, the connector comprising
a connector housing defining a port configured and arranged for receiving the proximal end portion of the at least one lead body of the paddle lead, and
a plurality of connector contacts disposed in the connector housing, the plurality of connector contacts configured and arranged to couple to at least one of the plurality of terminals disposed along the proximal end portion of the at least one lead body.

17. A method of implanting a paddle lead into a patient, the method comprising:
providing the multi-needle paddle lead introducer of claim 1;
inserting the at least one primary needle of the multi-needle paddle lead introducer into the patient;
advancing the distal tip of the at least one primary needle to a target insertion location in proximity to a target stimulation location within the patient;
advancing the at least one secondary needle of the multi-needle paddle lead introducer relative to the at least one primary needle until the distal tip of the at least one secondary needle is disposed at the target insertion location;
advancing a distal end portion of the sheath of the multi-needle paddle lead introducer to the target insertion location along the longitudinal lengths of the at least one primary needle and the at least one secondary needle;
removing the at least one primary needle and the at least one secondary needle from the patient while leaving the distal end portion of the sheath inserted into the target insertion location;
advancing a paddle lead along a lumen of the sheath to the target insertion location; and
removing the sheath from the patient leaving the paddle lead disposed in the patient.

18. The method of claim 17, further comprising inserting a stylet into a lumen of the at least one primary needle prior to inserting the at least one primary needle into the patient.

19. The method of claim 18, further comprising removing the stylet from the lumen of the at least one primary needle subsequent to advancing the distal tip of the at least one primary needle to the target insertion location.

20. The method of claim 17, further comprising performing a loss-of-resistance test prior to advancing the distal end portion of the sheath to the target insertion location.

* * * * *